United States Patent
Tzianabos et al.

(10) Patent No.: US 9,265,790 B2
(45) Date of Patent: Feb. 23, 2016

(54) ZWITTERIONIC IMMUNOMODULATORS FOR THE TREATMENT OF ASTHMA AND ALLERGY

(71) Applicant: The Brigham and Women's Hospital, Inc., Boston, MA (US)

(72) Inventors: Arthur O. Tzianabos, Reading, MA (US); Dennis L. Kasper, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 14/043,876

(22) Filed: Oct. 2, 2013

(65) Prior Publication Data

US 2014/0099331 A1    Apr. 10, 2014

Related U.S. Application Data

(63) Continuation of application No. 13/316,744, filed on Dec. 12, 2011, now abandoned, which is a continuation of application No. 12/754,948, filed on Apr. 6, 2010, now abandoned, which is a continuation of application No. 10/814,620, filed on Mar. 31, 2004, now abandoned.

(60) Provisional application No. 60/459,056, filed on Mar. 31, 2003.

(51) Int. Cl.
| | |
|---|---|
| *A01N 43/04* | (2006.01) |
| *A01N 63/02* | (2006.01) |
| *A61K 35/00* | (2006.01) |
| *A61K 39/02* | (2006.01) |
| *A61K 31/715* | (2006.01) |
| *A61K 45/00* | (2006.01) |
| *C07H 21/02* | (2006.01) |
| *A61K 31/726* | (2006.01) |
| *A61K 35/744* | (2015.01) |
| *A61K 38/16* | (2006.01) |
| *A61K 39/35* | (2006.01) |
| *A61K 45/06* | (2006.01) |
| *A61K 9/00* | (2006.01) |
| *A61K 39/00* | (2006.01) |

(52) U.S. Cl.
CPC ............. *A61K 31/726* (2013.01); *A61K 9/0075* (2013.01); *A61K 31/715* (2013.01); *A61K 35/744* (2013.01); *A61K 38/164* (2013.01); *A61K 39/35* (2013.01); *A61K 45/06* (2013.01); *A61K 2039/55583* (2013.01)

(58) Field of Classification Search
None
See application file for complete search history.

(56) References Cited

U.S. PATENT DOCUMENTS

| | | |
|---|---|---|
| 3,849,550 A | 11/1974 | Teitelbaum et al. |
| 4,619,995 A | 10/1986 | Hayes |
| 4,782,067 A | 11/1988 | Blythin et al. |
| 4,819,617 A | 4/1989 | Goldberg et al. |
| 4,835,252 A | 5/1989 | Musso et al. |
| 4,886,787 A | 12/1989 | de Belder et al. |
| 4,937,270 A | 6/1990 | Hamilton et al. |
| 5,126,141 A | 6/1992 | Henry |
| 5,130,417 A | 7/1992 | Stanley et al. |
| 5,140,016 A | 8/1992 | Goldberg et al. |
| 5,158,939 A | 10/1992 | Takayama et al. |
| 5,196,510 A | 3/1993 | Rodwell et al. |
| 5,215,896 A | 6/1993 | Keck et al. |
| 5,331,573 A | 7/1994 | Balaji et al. |
| 5,514,581 A | 5/1996 | Ferrari et al. |
| 5,532,221 A | 7/1996 | Huang et al. |
| 5,576,002 A | 11/1996 | Jennings et al. |
| 5,605,938 A | 2/1997 | Roufa et al. |
| 5,679,654 A | 10/1997 | Tzianabos et al. |
| 5,679,658 A | 10/1997 | Elson |
| 5,700,787 A | 12/1997 | Tzianabos et al. |
| 5,700,906 A | 12/1997 | Arnot et al. |
| 5,705,178 A | 1/1998 | Roufa et al. |
| 5,760,200 A | 6/1998 | Miller et al. |
| 5,888,741 A | 3/1999 | Hendry |
| 5,993,825 A | 11/1999 | Jennings et al. |
| 6,110,672 A | 8/2000 | Mandel et al. |
| 6,150,459 A | 11/2000 | Mayes et al. |
| 6,294,518 B1 | 9/2001 | Potter et al. |
| 6,447,765 B1 | 9/2002 | Horwitz |
| 6,670,146 B2 | 12/2003 | Barrat et al. |
| 6,995,237 B1 | 2/2006 | Zimmerman |
| 7,026,285 B2 * | 4/2006 | Tzianabos et al. ............. 514/9.4 |

(Continued)

FOREIGN PATENT DOCUMENTS

| | | |
|---|---|---|
| DE | 3704389 A1 | 8/1988 |
| EP | 1358885 A1 | 11/2003 |

(Continued)

OTHER PUBLICATIONS

Tang et al.; Th Type 1-stimulating activity of lung macrophages inhibits Th2-mediated allergic airway inflammation by an IFN-gamma dependent mechanism, J. Immunol., 166:1471-1481, 2001.*

(Continued)

*Primary Examiner* — Nora Rooney
(74) *Attorney, Agent, or Firm* — Wolf, Greenfield & Sacks, P.C.

(57) ABSTRACT

Methods and products for treating and protecting against asthma and allergic conditions are provided. The methods and products are related to certain naturally occurring and synthetic zwitterionic polymers which are found to induce certain T regulatory (Treg) cells and to exert immunosuppressive effects in vitro and in vivo.

9 Claims, 13 Drawing Sheets

(56) References Cited

U.S. PATENT DOCUMENTS

| | | | |
|---|---|---|---|
| 7,083,777 | B1 | 8/2006 | Tzianabos et al. |
| 7,163,683 | B2 | 1/2007 | Barstad et al. |
| 7,166,455 | B2 | 1/2007 | Comstock et al. |
| 7,629,330 | B2 | 12/2009 | Wang et al. |
| 7,678,558 | B2 | 3/2010 | Comstock et al. |
| 7,803,602 | B2 | 9/2010 | Comstock et al. |
| 8,008,276 | B2 | 8/2011 | Wang et al. |
| 8,206,726 | B2 | 6/2012 | Kasper et al. |
| 2001/0001788 | A1 | 5/2001 | Satoh et al. |
| 2002/0090357 | A1 | 7/2002 | Barrat et al. |
| 2003/0219413 | A1 | 11/2003 | Comstock et al. |
| 2004/0092433 | A1 | 5/2004 | Wang et al. |
| 2004/0219160 | A1 | 11/2004 | Tzianabos et al. |
| 2005/0119164 | A1* | 6/2005 | Taylor et al. ............ 514/8 |
| 2006/0153832 | A1 | 7/2006 | Tzianabos et al. |
| 2007/0020730 | A1 | 1/2007 | Comstock et al. |
| 2008/0057565 | A1 | 3/2008 | Comstock et al. |
| 2009/0124573 | A1 | 5/2009 | Mazmanian et al. |
| 2009/0317410 | A1 | 12/2009 | Wang et al. |
| 2009/0317427 | A1 | 12/2009 | Kasper et al. |
| 2010/0311686 | A1 | 12/2010 | Kasper et al. |
| 2011/0009360 | A1 | 1/2011 | Kasper et al. |
| 2011/0059125 | A1 | 3/2011 | Tzianabos et al. |
| 2011/0086011 | A1 | 4/2011 | Kasper et al. |
| 2012/0315264 | A1 | 12/2012 | Tzianabos et al. |

FOREIGN PATENT DOCUMENTS

| | | | | |
|---|---|---|---|---|
| EP | 1459757 | A1 | 9/2004 | |
| GB | 2286193 | | 8/1995 | |
| JP | 56128721 | | 10/1981 | |
| WO | WO 95/31990 | A1 | 11/1995 | |
| WO | WO 96/07427 | A1 | 3/1996 | |
| WO | WO 96/32119 | A1 | 10/1996 | |
| WO | WO 96/35433 | A1 | 11/1996 | |
| WO | WO 98/45335 | A1 | 10/1998 | |
| WO | WO 00/01733 | | 1/2000 | |
| WO | WO 00/59515 | * | 10/2000 | ........... A61K 31/088 |
| WO | WO 02/45708 | A2 | 6/2002 | |
| WO | WO 03/075953 | * | 9/2003 | ............ A61K 39/02 |
| WO | WO 03/077863 | | 9/2003 | |
| WO | WO 2004/089407 | | 10/2004 | |
| WO | WO 2007/092451 | A2 | 8/2007 | |
| WO | WO 2009/062132 | | 5/2009 | |

OTHER PUBLICATIONS

Rabe et al. 'Pharmacological treatment of asthma today.' Eur. Respir. J Suppl. 34:34s-40s, 2001.*
Johnson et al. 'Bacterial capsular polysaccharide prevents the onset of asthma through T-cell activation.' Glycobiology 1-8, 2014.*
International Search Report and Written Opinion for Application No. PCT/US07/03160, mailed Jan. 28, 2008.
International Preliminary Report on Patentability for Application No. PCT/US07/03160, mailed Aug. 12, 2008.
International Preliminary Examination Report for Application No. PCT/US00/08586, mailed Jun. 29, 2001.
International Search Report for Application No. PCT/US00/08586, mailed Nov. 7, 2000.
Written Opinion for Application No. PCT/US00/08586, mailed Jan. 26, 2001.
International Preliminary Examination Report for Application No. PCT/US95/11160, mailed Nov. 21, 1996.
Written Opinion for Application No. PCT/US95/11160, mailed Jun. 19, 1996.
International Search Report for Application No. PCT/US95/11160, mailed Jan. 8, 1996.
International Search Report and Written Opinion for Application No. PCT/US2004/009838, mailed Oct. 25, 2004.
International Preliminary Report on Patentability for Application No. PCT/US2004/009838, mailed Oct. 1, 2005.
International Preliminary Examination Report for Application No. PCT/US01/47251, mailed Oct. 29, 2004.
International Search Report for Application No. PCT/US01/47251, mailed Oct. 11, 2002.
Invitation to Pay Additional Fees for Application No. PCT/US01/47251, mailed Jul. 29, 2002.
Partial European Search Report for Application No. EP04014020.4, mailed Aug. 4, 2004.
Partial European Search Report for Application No. EP05110973.4, mailed Feb. 22, 2006.
NCBI Sequence View "Toxin" [*Salmonella typhimurium* LT2]. http://www.ncbi.nim.nih.gov/entrez/viewer.fcgi?db=protein&id=17233414, pp. 1-2. 2007.
No Author Listed, Acute Respiratory Disease Syndrome: What is acute respiratory disease syndrome? American Lung Association. 3 pages. http://www.lungusa.org/site/apps/nlnet/content3.aspz?c=dvLUK9O0E&b=2058817&content. Sep. 24, 2008.
No Author Listed, Lupus study. Meet a Lupus Researcher. www.lupusstudy.org/updates.php. Nov. 1-2, 2005.
No Author Listed, Polyethylene Glycols (PEGs). Accessed Mar. 7, 2005. 1 page. http://www.mindfully.org/Plastic/Polymers/Polyethylene-Glycols-PEGs.htm.
No Author Listed, The Merck Index . Eleventh Edition 1989:734-735.
No Author Listed, VAXA, Systemic lupus erythematosus (SLE), damaging and unpredictable. http://www.vaxa.com/arthritis-systemic-lupus-erythematosus.cfm. 1 page. Accessed Apr. 3, 2008.
Aharoni et al., Bystander suppression of experimental autoimmune encephalomyelitis by T cell lines and clones of the Th2 type induced by copolymer 1. J Neuroimmunol. Nov. 2, 1998;91(1-2):135-46.
Aharoni et al., Copolymer 1 induces T cells of the T helper type 2 that crossreact with myelin basic protein and suppress experimental autoimmune encephalomyelitis. Proc Natl Acad Sci U S A. Sep. 30, 1997;94(20):10821-6.
Aharoni et al., Studies on the mechanism and specificity of the effect of the synthetic random copolymer GLAT on graft-versus-host disease. Immunol Lett. Jul. 1997;58(2):79-87.
Akbari O et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Arnon et al., New insights into the mechanism of action of copolymer 1 in experimental allergic encephalomyelitis and multiple sclerosis. J Neurol. Apr. 1996;243(4 Suppl 1):S8-13. Review.
Azzawi et al., Identification of activated T lymphocytes and eosinophils in bronchial biopsies in stable atopic asthma. Am Rev Respir Dis. Dec. 1990;142(6 Pt 1):1407-13.
Barnes et al., Regulatory T cells reinforce intestinal homeostasis. Immunity. Sep. 18, 2009;31(3):401-11. doi: 10.1016/j.immuni.2009.08.011.
Barrat FJ et al., In vitro generation of interleukin 10-producing regulatory CD4(+) T cells is induced by immunosuppressive drugs and inhibited by T helper type 1 (Th1)- and Th2-inducing cytokines. J Exp Med. Mar. 4, 2002;195(5):603-16.
Barutca et al., Prevention of interleukin-2-induced severe bronchospasm with salbutamol. J Aerosol Med. 2003 Summer;16(2):183-4.
Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.
Batta et al., Conformational stabilization of the altruronic acid residue in the O-specific polysaccharide of Shigella sonnei/Plesiomonas shigelloides. Carbohydr Res. Dec. 1997;305(1):93-9.
Baumann H et al., Structural elucidation of two capsular polysaccharides from one strain of Bacteroides fragilis using high-resolution NMR spectroscopy. Biochemistry. Apr. 28, 1992;31(16):4081-9.
Bazan et al., Unraveling the structure of IL-2. Science. Jul. 17, 1992;257(5068):410-3.
Bernatowska-Matuszkiewicz et al., IgG subclasses and antibody response to pneumococcal capsular polysaccharides in children with severe sinopulmonary infections and asthma. Immunol Invest. Apr. 1991;20(2):173-85.
Biló et al., Diagnosis of Hymenoptera venom allergy. Allergy. Nov. 2005;60(11):1339-49.
Boes et al., Accelerated development of IgG autoantibodies and autoimmune disease in the absence of secreted IgM. Proc Natl Acad Sci U S A. Feb. 1, 2000;97(3):1184-9.

(56) References Cited

OTHER PUBLICATIONS

Boguniewicz, The autoimmune nature of chronic urticaria. Allergy Asthma Proc. Sep.-Oct. 2008;29(5):433-8. doi: 10.2500/aap.2008.29.3148.
Brubaker Jo et al., Mitogenic activity of purified capsular polysaccharide A from Bacteroides fragilis: differential stimulatory effect on mouse and rat lymphocytes in vitro. J Immunol Feb. 15, 1999;162(4):2235-42.
Büdinger et al., Immunologic mechanisms in hypersensitivity reactions to metal ions: an overview. Allergy. Feb. 2000;55(2):108-15. Review.
Cobb et al., Zwitterionic capsular polysaccharides: the new MHCII-dependent antigens, Cell Microbiol., 2005, 7(10):1398-1403.
Comstock et al., Interstrain variation of the polysaccharide B biosynthesis locus of Bacteroides fragilis: characterization of the region from strain 638R. J Bacteriol. Oct. 1999;181(19):6192-6.
Comstock et al.; Bacterial Glycans: Key Mediators of Diverse Host Immune Responses; Cell; Sep. 8, 2006, 126: 847-850.
Conesa et al., Interleukin-2 induces peroxide production by primed normodense eosinophils of patients with asthma. Allergy Asthma Proc. Jan.-Feb. 2003;24(1):27-33.
Coyne et al., Bacteroides fragilis NCTC9343 produces at least three distinct capsular polysaccharides: cloning, characterization, and reassignment of polysaccharide B and C biosynthesis loci. Infect Immun. Nov. 2000;68(11):6176-81.
Crabb et al., T cell regulation of Bacteroides fragilis-induced intraabdominal abscesses. Rev Infect Dis. Jan.-Feb. 1990;12 Suppl 2:S178-84. Review.
Craig, Autologous hematopoietic stem cell transplantation for Crohn's disease. Autoimmun Rev. Aug. 2002;1(4):244-9. Review.
Dahiyat et al., De novo protein design: fully automated sequence selection. Science. Oct. 3, 1997;278(5335):82-7.
Difabio JL et al., Structure of the capsular polysaccharide antigen of type IV group B *Streptococcus*. Can. J. Chem. 1989; 67: 877-882.
Finberg RW et al., Decay-accelerating factor expression on either effector or target cells inhibits cytotoxicity by human natural killer cells. J Immunol Sep. 15, 1992;149(6):2055-60.
Fournier JM et al., Isolation of type 5 capsular polysaccharide from *Staphylococcus aureus*. Ann Inst Pasteur Microbiol. Sep.-Oct. 1987;138(5):561-7.
Fridkis-Hareli et al., Binding motifs of copolymer 1 to multiple sclerosis- and rheumatoid arthritis-associated HLA-DR molecules. J Immunol. Apr. 15, 1999;162(8):4697-704.
Fridkis-Hareli et al., Binding of random copolymers of three amino acids to class II MHC molecules. Int Immunol. May 1999;11(5):635-41.
Fridkis-Hareli et al., Direct binding of myelin basic protein and synthetic copolymer 1 to class II major histocompatibility complex molecules on living antigen-presenting cells—specificity and promiscuity. Proc Natl Acad Sci U S A. May 24, 1994;91(11):4872-6.
Fridkis-Hareli et al., Synthetic copolymer 1 and myelin basic protein do not require processing prior to binding to class II major histocompatibility complex molecules on living antigen-presenting cells. Cell Immunol. Jul. 1955;163(2):229-36.
Gelu-Simeon, et al., Evaluation and predictive factors of thyroid disorder due to interferon alpha in the treatment of hepatitis C, World J Gastroenterol 2009; 15(3):328-333.
Genbank Accession No. AJ277832; Hutloff; Jan. 19, 2001.
Genbank Accession No. CAC06612; Hutloff; Jan. 19, 2001.
Genbank Accession No. NM_012092; Dec. 20, 2003.
Genbank Accession No. NP_036224; Dec. 20, 2003.
Gibson et al., Cellular mechanism of intraabdominal abscess formation by Bacteroides fragilis. J Immunol May 15, 1998;160(10):5000-6.
Gibson et al., The capsular polysaccharide complex of Bacteroides fragilis induces cytokine production from human and murine phagocytic cells. Infect Immun. Mar. 1996;64(3):1065-9.
Glazebrook J et al., A novel exopolysaccharide can function in place of the calcofluor-binding exopolysaccharide in nodulation of alfalfa by Rhizobium meliloti. Cell. Feb. 24, 1989;56(4):661-72.
Golgher et al., Galactofuranose-containing glycoconjugates of epimastigote and trypomastigote forms of Trypanosoma cruzi. Mol Biochem Parasitol. Aug. 1993;60(2):249-64.
Gonzalez-Hernandex et al., Peripheral Blood CD161+ T cells from Asthmatic Patients are Activated During Asthma Attack and Predominantly Produce IFN-Gamm, Scand. J. Immunol., 2007, 65: 368-375.
Greenberger, 8. Drug allergy. J Allergy Clin Immunol Feb. 2006;117(2 Suppl Mini-Primer):S464-70.
Groux H et al., A CD4+ T-cell subset inhibits antigen-specific T-cell responses and prevents colitis. Nature. Oct. 16, 1997;389(6652):737-42.
Groux H, Type 1 T-regulatory cells: their role in the control of immune responses. Transplantation. May 15, 2003;75(9 Suppl):8S-12S.
Hafler et al., Anti-CD4 and anti-CD2 monoclonal antibody infusions in subjects with multiple sclerosis. Immunosuppressive effects and human anti-mouse responses. J Immunol Jul. 1, 1988;141(1):131-8.
Hamelmann E et al., Noninvasive measurement of airway responsiveness in allergic mice using barometric plethysmography. Am J Respir Crit Care Med. Sep. 1997;156(3 Pt 1):766-75.
Haregewoin A et al., Human gamma delta+ T cells respond to mycobacterial heat-shock protein. Nature. Jul. 27, 1989;340(6231):309-12.
Hertl et al., Immunologic mechanisms in hypersensitivity reactions to metal ions: an overview, Allergy, 2000, 55:108-115.
Hertl et al., T cell control in autoimmune bullous skin disorders. J Clin Invest. May 2006;116(5):1159-66. Review.
Hirata et al., Cytokine synthesis of human monocytes stimulated by triple or single helical conformer of an antitumour (1→3)-beta-D-glucan preparation, sonifilan. Zentralbl Bakteriol. Nov. 1998;288(3):403-13.
Hutloff A et al., ICOS is an inducible T-cell co-stimulator structurally and functionally related to CD28. Nature. Jan. 21, 1999;397(6716):263-6.
Itokazu et al., Abscess formation as a complication caused by postoperative osteomyelitis of the femur. Arch Orthop Trauma Surg. 1998;118(1-2):99-102. Review.
Jennings et al., Immunochemistry of groups A, B, and C meningococcal polysaccharide-tetanus toxoid conjugates. J Immunol Sep. 1981;127(3):1011-8.
Jennings et al., Induction of meningococcal group B polysaccharide-specific IgG antibodies in mice by using an N-propionylated B polysaccharide-tetanus toxoid conjugate vaccine. J Immunol Sep. 1, 1986;137(5):1708-13.
Jennings HJ et al., Structure of the complex polysaccharide C-substance from *Streptococcus pneumoniae* type 1. Biochemistry. Sep. 30, 1980;19(20):4712-9.
Johnson et al., Bacterial capsular polysaccharide prevents the onset of asthma through T-cell activation. Glycobiology. Apr. 2015;25(4):368-75. doi: 10.1093/glycob/cwu117. Epub Oct. 27, 2014.
Jonuleit H et al., Identification and functional characterization of human CD4(+)CD25(+) T cells with regulatory properties isolated from peripheral blood. J Exp Med. Jun. 4, 2001;193(11):1285-94.
Jonuleit H et al., The regulatory T cell family: distinct subsets and their interrelations. J Immunol Dec. 15, 2003;171(12):6323-7.
Jotwani et al., Pathogenicity of Bacteroides fragilis group in rat intra-abdominal abscesses. Microbiol Immunol. 1992;36(10):1041-9.
Jyonouchi, Non-IgE mediated food allergy—update of recent progress in mucosal immunity. Inflamm Allergy Drug Targets. Oct. 2012;11(5):382-96.
Kalka-Moll et al., Bacteriodes Fragilis NCTC 9343 Capsular Polysaccharide PS A and the Effect of Chain Length of T cell Proliferation. Abstracts of the 98th Gen Mtg of the American Soc for Microbiol. 1998;98:123. Abstract B-405.
Kalka-Moll WM et al., Effect of molecular size on the ability of zwitterionic polysaccharides to stimulate cellular immunity. J Immunol. Jan. 15, 2000;164(2):719-24.
Kalka-Moll WM et al., Immunochemical and biological characterization of three capsular polysaccharides from a single Bacteroides fragilis strain. Infect Immun. Apr. 2001;69(4):2339-44.
Kalka-Moll, et al.; Zwitterionic Polysaccharides Stimulate T Cells by MHC Class II-Dependent Interactions; J. Immunol. ; 2002; 169: 6149-6153.
Kasper et al., Capsular polysaccharides and lipopolysaccharides from two Bacteroides fragilis reference strains: chemical and immunochemical characterization. J Bacteriol. Feb. 1983;153(2):991-7.

(56) References Cited

OTHER PUBLICATIONS

Kasper et al., Protective efficacy of immunization with capsular antigen against experimental infection with Bacteroides fragilis. J Infect Dis. Nov. 1979;140(5):724-31.
Kasper et al., Surface antigens as virulence factors in infection with Bacteroides fragilis. Rev Infect Dis. Mar.-Apr. 1979;1(2):278-90.
Kasper et al., The polysaccharide capsule of *Bacteroides fragilis* subspecies fragilis: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kenne L et al., Structural studies of the O-specific side-chains of the shigella sonnei phase I lipopolysaccharide. Carbohydr. Res. Jan. 1, 1980;78(1):119-26.
Kennedy R et al., Prevention of experimental postoperative peritoneal adhesions by N,O-carboxymethyl chitosan. Surgery. Nov. 1996;120(5):866-70.
Knetsch et al., Polymers with tunable toxicity: a reference scale for cytotoxicity testing of biomaterial surfaces. J Biomed Mater Res A. Sep. 15, 2007;82(4):947-57.
Knirel et al., The structure of O-specific polysaccharides and serological classification of Pseudomonas aeruginosa (a review). Acta Microbiol Hung. 1988;35(1):3-24. Review.
Knirel Y A et al., Somatic antigens of Pseudomonas aeruginosa. The structure of O-specific polysaccharide chains of lipopolysaccharides of P. aeruginosa O3 (Lanyi), O25 (Wokatsch) and Fisher immunotypes 3 and 7. Eur J Biochem. Sep. 15, 1987;167(3):549-61.
Kormelink, et al., Atopic and non-atopic allergic disorders: current insights into the possible involvement of free immunoglobulin light chains. Clin Exp Allergy. Jan. 2009;39(1):33-42. doi: 10.1111/j.1365-2222.2008.03135.x. Epub Nov. 17, 2008.
Krause et al., An inhibitor of cell proliferation associated with adhesion formation is suppressed by N,O-carboxymethyl chitosan. J Invest Surg. Mar.-Apr. 1998;11(2):105-13.
Kulicke et al., Correlation between immunological activity, molar mass, and molecular structure of different (1→3)-beta-D-glucans. Carbohydr Res. Jan. 2, 1997;297(2):135-43.
Kurup et al., Antibody response to low-molecular-weight antigens of Aspergillus fumigatus in allergic bronchopulmonary aspergillosis. J Clin Microbiol. Jun. 1989;27(6):1312-6.
Lindberg B et al., Structural studies of the capsular polysaccharide from *Streptococcus pneumoniae* type 1. Carbohydr. Res. Jan. 1, 1980;78(1):111-7.
Lindberg et al., Virulence factors in infections with bacteroides fragilis: isolation and characterization of capsular polysaccharide and lipopolysaccharide. Scand J Infect Dis Suppl. 1982;35:45-52.
Maconi et al., Contrast radiology, computed 10omography, and ultrasonography in detecting internal fistulas and intra-abdominal abscesses in Chrohn's disease: a prospective comparative study. Amer J Gast. 2003;98(7):1545-1555.
Mäkelä MJ et al., IL-10 is necessary for the expression of airway hyperresponsiveness but not pulmonary inflammation after allergic sensitization. Proc Natl Acad Sci U S A. May 23, 2000;97(11):6007-12.
Mamessier et al., Cytokines in atopic diseases: revisiting the Th2 dogma, Eur. J. Dermatol., 2006, 162(2):103-113.
Mazmanian et al., The love-hate relationship between bacterial polysaccharides and the host immune system, Nature, 2006, 6:849-858.
Mazmanian et al.; An Immunomodulatory Molecule of Symbiotic Bacteria Directs Maturation of the Host Immune System; Cell; Jul. 15, 2005; vol. 122: 107-118.
Meisel-Mikolajczyk et al., Human T cell adhesion to endothelium stimulated by membrane components extracted from strains of Bacteroides vulgatus (member of B. fragilis group). Arch Immunol Ther Exp (Warsz). 1993;41(2):129-31.
Miller et al., Severe asthma and the omalizumab option, Clinical and Molecular Allergy, 2008, 6(4):1-13.
Mojtabavi N et al., Long-lived Th2 memory in experimental allergic asthma. J Immunol Nov. 1, 2002;169(9):4788-96.
Montz et al., Interleukin 10: ability to minimize postoperative intraperitoneal adhesion formation in a murine model. Fertil Steril. Jun. 1994;61(6):1136-40.

Moore, The List Goes on, New Additions to the Autoimmune Disease Roster. http://autoimmunedisease.suite101.com/blog.cfm/the_list_goes_on. pp. 1-3.
Mulholland et al., Strategies for the control of pneumococcal diseases. Vaccine. Jul. 30, 1999;17 Suppl 1:S79-84. Review.
Nielsen et al., Applications of peptide nucleic acids. Curr Opin Biotechnol. Feb. 1999;10(1):71-5. Review.
Norman, Thyroiditis—Inflammation of the thyroid gland, Endocrineweb 2009; www.endocrineweb.com/throiditis.html, 1-4. Downloaded Jul. 28, 2009.
Oh JW et al., CD4 T-helper cells engineered to produce IL-10 prevent allergen-induced airway hyperreactivity and inflammation. J Allergy Clin Immunol. Sep. 2002;110(3):460-8.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1→3)-beta-D-glucans in mice. Biol Pharm Bull. Jan. 1995;18(1):126-33.
Onderdonk AB et al., Evidence for T cell-dependent immunity to Bacteroides fragilis in an intraabdominal abscess model. J Clin Invest. Jan. 1982;69(1):9-16.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Pantosti A et al., Immunochemical characterization of two surface polysaccharides of Bacteroides fragilis. Infect Immun. Jun. 1991;59(6):2075-82.
Pantosti et al., Bacteroides fragilis strains express multiple capsular polysaccharides. J Clin Microbiol. Jul. 1993;31(7):1850-5.
Paoletti et al., Effects of chain length on the immunogenicity in rabbits of group B *Streptococcus* type III oligosaccharide-tetanus toxoid conjugates. J Clin Invest. Jan. 1992;89(1):203-9.
Park et al., Interleukin-2 and soluble interleukin-2 receptor in bronchoalveolar lavage fluid from patients with bronchial asthma. Chest. Aug. 1994;106(2):400-6.
Pavliak et al., Structural elucidation of the capsular polysaccharide of Bacteroides fragilis strain 23745M1. Carbohydr Res. Oct. 2, 1995;275(2):333-41.
Perumal et al., Protective effect of interleukin-2 on experimental intra-abdominal abscess development due to Bacteriodes Fragilis. Clinical Research. 1990;38(2):550A.
Poonawalla et al., Urticaria : a review. Am J Clin Dermatol. 2009;10(1):9-21. doi: 10.2165/0128071-200910010-00002.
Ranua et al., Serum IgA, IgG, and IgM concentrations in patients with epilepsy and matched controls: a cohort-based cross-sectional study. Epilepsy Behav. Mar. 2005;6(2):191-5.
Reed et al., A simple method of estimating fifty percent endpoints. Am J Hyg. 1938;27:493-497.
Riesenfeld et al., Biosynthesis of heparin. Assay and properties of the microsomal N-acetyl-D-glucosaminyl N-deacetylase.J Biol Chem. Feb. 10, 1980;255(3):922-8.
Roncarolo MG et al., Type 1 T regulatory cells. Immunol Rev. Aug. 2001;182:68-79.
Rypens et al., Percutaneous drainage of abdominal abscesses in pediatric Crohn's disease. AJR Am J Roentgenol. Feb. 2007;188(2):579-85.
Schlegel et al., A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo. Proc Natl Acad Sci U S A. May 14, 1996;93(10):5061-6. Erratum in: Proc Natl Acad Sci U S A Aug. 6, 1996;93(16):8796.
Schneider et al., De novo design of molecular architectures by evolutionary assembly of drug-derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from Trimeresurus wagleri which blocks the nicotinic acetylcholine receptor. Biophys J. Jan. 1996;70(1):3-13.

(56) References Cited

OTHER PUBLICATIONS

Shaklee and Conrad; "Hydrazinolysis of heparin and other glycosaminoglycans"; Biochem. J. (1984); 217: 187-197.
Shapiro et al., Cellular control of abscess formation: role of T cells in the regulation of abscesses formed in response to Bacteroides fragilis. J Immunol Jul. 1, 1986;137(1):341-6.
Shapiro et al., Cellular immunity to Bacteroides fragilis capsular polysaccharide. J Exp Med. Apr. 1, 1982;155(4):1188-97.
Sharpe AH et al., The B7-CD28 superfamily. Nat Rev Immunol Feb. 2002;2(2):116-26.
Shevach EM, CD4+ CD25+ suppressor T cells: more questions than answers. Nat Rev Immunol. Jun. 2002;2(6):389-400.
Simmons et al., Synthesis and membrane permeability of PNA-peptide conjugates. Bioorg Med Chem Lett. 1997;7(23):3001-6.
Stein et al., Thymus-independent and thymus-dependent responses to polysaccharide antigens. J Infect Dis. Jun. 1992;165 Suppl 1:S49-52. Review.
Suri-Payer E et al., CD4+CD25+ T cells inhibit both the induction and effector function of autoreactive T cells and represent a unique lineage of immunoregulatory cells. J Immunol. Feb. 1, 1998;160(3):1212-8.
Szu SC et al., Relation between structure and immunologic properties of the Vi capsular polysaccharide. Infect Immun. Dec. 1991;59(12):4555-61.
Taylor RL et al., Stoichiometric depolymerization of polyuronides and glycosaminoglycuronans to monosaccharides following reduction of their carbodiimide-activated carboxyl groups. Biochemistry. Apr. 11, 1972;11(8):1383-8.
Teitelbaum et al., Immunomodulation of experimental autoimmune encephalomyelitis by oral administration of copolymer 1. Proc Natl Acad Sci U S A. Mar. 30, 1999;96(7):3842-7.
Teitelbaum et al., Specific inhibition of the T-cell response to myelin basic protein by the synthetic copolymer Cop 1. Proc Natl Acad Sci U S A. Dec. 1988;85(24):9724-8.
Teitelbaum et al., Synthetic copolymer 1 inhibits human T-cell lines specific for myelin basic protein. Proc Natl Acad Sci U S A. Jan. 1, 1992;89(1):137-41.
Teitelbaum et al., Unprimed spleen cell populations recognize macrophage-bound antigen with opposite net electric charge. Proc Natl Acad Sci U S A. Apr. 1977;74(4):1693-6.
Thomas et al., Randomised controlled trial of short bursts of a potent topical corticosteroid versus prolonged use of a mild preparation for children with mild or moderate atopic eczema. BMJ. Mar. 30, 2002;324(7340):768.
Tournoy KG et al., Endogenous interleukin-10 suppresses allergen-induced airway inflammation and nonspecific airway responsiveness. Clin Exp Allergy. Jun. 2000;30(6):775-83.
Tzianabos AO et al., Polysaccharide-mediated protection against abscess formation in experimental intra-abdominal sepsis. J Clin Invest. Dec. 1995;96(6):2727-31.
Tzianabos AO et al., Structural characteristics of polysaccharides that induce protection against intra-abdominal abscess formation. Infect Immun. Nov. 1994;62(11):4881-6.
Tzianabos AO et al., Structural features of polysaccharides that induce intra-abdominal abscesses. Science. Oct. 15, 1993;262(5132):416-9.
Tzianabos AO et al., Structural rationale for the modulation of abscess formation by *Staphylococcus aureus* capsular polysaccharides. Proc Natl Acad Sci U S A. Jul. 31, 2001;98(16):9365-70. Epub Jul. 24, 2001.
Tzianabos AO et al., T cells activated by zwitterionic molecules prevent abscesses induced by pathogenic bacteria. J Biol Chem. Mar. 10, 2000;275(10):6733-40.
Tzianabos AO et al., The capsular polysaccharide of Bacteroides fragilis comprises two ionically linked polysaccharides. J Biol Chem. Sep. 5, 1992;267(25):18230-5.
Tzianabos et al., Bacterial structure and functional relation to abscess formation. Infect Agents Dis. Oct. 1994;3(5):256-65. Review.
Tzianabos et al., Characteristics of bacterial polysaccharides that activate T cells. The International Carbohydrate Symposium XVII. Jul. 21, 1994.
Tzianabos et al., Effect of surgical adhesion reduction devices on the propagation of experimental intra-abdominal infection. Arch Surg. Nov. 1999;134(11):1254-9.
Tzianabos et al., IL-2 mediates protection against abscess formation in an experimental model of sepsis. J Immunol. Jul. 15, 1999;163(2):893-7.
Tzianabos et al., Protection against experimental intraabdominal sepsis by two polysaccharide immunomodulators. J Infect Dis. Jul. 1998;178(1):200-6.
Tzianabos et al., Structural basis for polysaccharide-mediated protection against intraabdominal abscess formation. 94th ASM General Meeting. May 23-27, 1994. Las Vegas, Nevada. Abstract B-206:65.
Tzianabos et al., Structure and function of Bacteroides fragilis capsular polysaccharides: relationship to induction and prevention of abscesses. Clin Infect Dis. Jun. 1995;20 Suppl 2:S132-40. Review.
Tzianabos et al., Structure-function relationships for polysaccharide-induced intra-abdominal abscesses. Infect Immun. Aug. 1994;62(8):3590-3.
Tzianabos et al., T Cell Activation by Zwitterionic polysaccharides and peptide mimetics prevents antrabdominal abscess formation. Abstracts of the 99th General Meeting of the American Society for Microbiology. Chicago, US: May 30-Jun. 3, 1999. Jun. 28, 1999;99:37-38.
Van Scott MR et al., IL-10 reduces Th2 cytokine production and eosinophilia but augments airway reactivity in allergic mice. Am J Physiol Lung Cell Mol Physiol. Apr. 2000;278(4):L667-74.
Vann WF et al., The structure of the capsular polysaccharide (K5 antigen) of urinary-tract-infective *Escherichia coli* 010:K5:H4. A polymer similar to desulfo-heparin. Eur J Biochem. May 15, 1981;116(2):359-64.
Velez et al., Type I *Streptococcus pneumonia* carbohydrate utilizes a nitric oxide and MHC II-dependent pathway for antigen presentation. Immunology. May 2009;127(1):73-82. doi:10.1111/j.1365-2567.2008.02924.x.
Viret et al., Molecular cloning and characterization of the genetic determinants that express the complete Shigella serotype D (Shigella sonnei) lipopolysaccharide in heterologous live attenuated vaccine strains. Mol Microbiol. Jan. 1993;7(2):239-52.
Wang et al., Structure characterization of an abscessogenic capsular polysaccharide from Bacteriodes fragilis by NMR spectroscopy. XIX International Conference of NMR in Biological Systems. Florence, Italy. Aug. 20-25, 2000. Abstract.
Wang Y et al., Structural basis of the abscess-modulating polysaccharide A2 from Bacteroides fragilis. Proc Natl Acad Sci U S A. Dec. 5, 2000;97(25):13478-83.
Wehr et al., Anti-low-density lipoprotein antibodies in alcoholics without and with liver disease and in social drinkers. Alcohol Alcohol. Jan.-Feb. 1997;32(1):43-9.
Wessels MR et al., Structure and immunochemistry of an oligosaccharide repeating unit of the capsular polysaccharide of type III group B *Streptococcus*. A revised structure for the type III group B streptococcal polysaccharide antigen. J Biol Chem. Jun. 15, 1987;262(17):8262-7.
Wujek et al., A carbohydrate polymer that effectively prevents epidural fibrosis at laminectomy sites in the rat. Exp Neurol. Nov. 1991;114(2):237-45.
Yokoyama et al., Adhesion behavior of rat lymphocytes to poly(ether)-poly(amino acid) block and graft copolymers. J Biomed Mater Res. Sep. 1986;20(7):867-78.
Yoshii, Cytotoxic effects of acrylates and methacrylates: relationships of monomer structures and cytotoxicity. J Biomed Mater Res. Dec. 15, 1997;37(4):517-24.
Zaleznik et al., A soluble suppressor T cell factor protects against experimental intraabdominal abscesses. J Clin Invest. Mar. 1985;75(3):1023-7.
Zhu et al., Oral administration of type-II collagen peptide 250-270 suppresses specific cellular and humoral immune response in collagen-induced arthritis. Clin Immunol. Jan. 2007;122(1):75-84. Epub Oct. 11, 2006.

* cited by examiner

ZWITTERIONIC IMMUNOMODULATORS FOR THE TREATMENT OF ASTHMA AND ALLERGY

RELATED APPLICATION

This application is a continuation of U.S. patent application Ser. No. 13/316,744, filed on Dec. 12, 2011, currently pending, which is a continuation of U.S. patent application Ser. No. 12/754,948, filed on Apr. 6, 2010, currently abandoned, which is a continuation of U.S. patent application Ser. No. 10/814,620, filed on Mar. 31, 2004, currently abandoned, which claims the benefit under 35 U.S.C. 119(e) of U.S. provisional patent application Ser. No. 60/459,056, filed Mar. 31, 2003, the entire contents of each of which is incorporated herein by reference.

FIELD OF THE INVENTION

The present invention relates to the field of immunology. More particularly, the invention relates to methods and compositions useful for inhibiting an immune response. The invention provides methods, uses, and compositions involving immunomodulatory zwitterionic polymers for the induction of T regulatory cells and the treatment of asthma and allergy.

BACKGROUND OF THE INVENTION

Certain polysaccharides purified from the surface of bacterial cells exhibit protective effects in vivo when tested in models of inflammation such as the formation of intraabdominal abscesses, intraabdominal sepsis, and post-surgical adhesions. U.S. Pat. Nos. 5,679,654 and 5,700,787; published international patent applications WO 96/07427, WO 00/59515, and WO 02/45708). When purified from whole capsule, certain polysaccharides derived from *Bacteroides fragilis, Staphylococcus aureus*, and *Streptococcus pneumoniae* have unique characteristics that set them apart from many polysaccharide antigens. These molecules are high molecular weight, helical, and zwitterionic in nature. Wang Y et al. (2000) *Proc Natl Acad Sci USA* 97:13478-81; Brubaker J O et al. (1999) *J Immunol* 162:2235-42; Tzianabos A O et al. (1995) *Infect Immun* 62:4881-6; Tzianabos A O et al. (1995) *J Clin Invest* 96:2727-31; Kalka-Moll W M et al. (2000) *J Immunol* 164:719-24; Tzianabos A O et al. (2000) *J Biol Chem* 275:6733-40.

Most bacterial polysaccharides are neutral or negatively charged and are considered to be T-cell-independent antigens. Abbas A K et al. (2003) *Cellular and Molecular Immunology*, Saunders, Philadelphia. It has been suggested, however, that the zwitterionic nature of these polysaccharides somehow involves them in interaction with $CD4^+$ T cells. Tzianabos A O et al. (1993) *Science* 262:416-9; Tzianabos A O et al. (2001) *Proc Natl Acad Sci USA* 98:9365-70. That zwitterionic polysaccharides activate $CD4^+$ T cells in vitro is supported by their reported ability to stimulate T-cell proliferation and the production of the cytokines IL-2, IFN-γ, and IL-10. In addition, it has been reported that the protective effect is adoptively transferred by polysaccharide-stimulated T cells in vivo. Published international patent application WO 00/59515; Kalka-Moll W M et al. (2000) *J Immunol* 164:719-24; Tzianabos A O et al. (2000) *J Biol Chem* 275:6733-8. It remains unclear, however, exactly how these molecules activate T cells or how they exert their protective effects.

SUMMARY OF THE INVENTION

Methods and products for treating and protecting against asthma and allergic conditions are provided. The methods and compositions are related, in part, to the discovery by the inventors of the ability of certain zwitterionic polymers, including certain capsular polysaccharides and synthetic peptides, to induce ICOS on CD4+ T lymphocytes and to promote the development of regulatory T lymphocytes (Treg cells). As disclosed herein, the Treg cells that are inducible by the zwitterionic polymers can confer and transfer protection against a number of inflammatory and allergic conditions, including abscess and adhesion formation, inflammatory bowel disease, and airway hyperresponsiveness (asthma).

It was unexpectedly discovered, according to the instant invention, that certain zwitterionic polymers induce ICOS on CD4+ T cells and promote the development of Treg cells. Others have previously reported that IL-10-secreting Treg cells can be generated by culturing T cells in the presence of exogenously supplied IL-10, immature dendritic cells (DC), or certain immunosuppressive drugs, notably $1,25(OH)_2$-vitamin D3 and dexamethasone. Groux H et al. (1997) *Nature* 389:737-42; Jonuleit H et al. (2001) *J Exp Med* 193:1285-94; Barrat F J et al. (2002) *J Exp Med* 195:603-16. None of these previous reports disclosed or suggested that the zwitterionic polymers of the invention could be used to induce ICOS expression or promote the development of Treg cells.

While it was already appreciated that the zwitterionic polymers could promote secretion of IL-10, the source and the significance of the IL-10 was not known. In addition, because IL-10 is widely recognized to be a highly pleiotropic cytokine, the context of the IL-10 secretion is highly significant. For example, it has been reported that IL-10 alone can either exacerbate or treat asthma. The significance of the ability of the zwitterionic polymers further to induce ICOS lies in the reportedly crucial role of ICOS-ICOSL signaling, in the presence of IL-10, in the development of Treg cells. Akbari O et al. (2002) *Nat Med* 8:1024-32. The Treg cells, in addition to being a source of IL-10, are believed to play an important role in the invention.

It was also unexpectedly found according to the instant invention that zwitterionic polysaccharide polymers can induce a cross-protective effect against peptide allergens.

In addition, it was unexpectedly discovered according to the instant invention that zwitterionic peptide polymers can induce a cross-protective effect against seemingly unrelated peptide allergens.

In one aspect the invention provides a method for treating an allergic condition other than asthma in a subject. The method according to this aspect involves administering to a subject having an allergic condition other than asthma an isolated polymer in an effective amount to treat the allergic condition, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In one embodiment the motif is a positively charged free amino moiety and a negatively charged moiety selected from the group consisting of phosphate, phosphonate, sulfate, and sulfonate.

In one embodiment the subject is free of symptoms otherwise calling for treatment with the polymer.

In one embodiment according to this aspect of the invention the administering involves delivering an aerosol of the polymer to an airway of the subject.

In one embodiment the method further includes administering to the subject an anti-allergy medicament selected from the group consisting of glucocorticoids, antihistamines, and anti-IgE. In various embodiments the anti-allergy medicament is prednisone, methylprednisolone, chlorcyclizine, chlorpheniramine, diphenhydramine hydrochloride (BENADRYL®, Parke-Davis), fexofenadine hydrochloride (ALLEGRA®, Aventis), hydroxyzine hydrochloride (ATARAX®, Pfizer), loratadine (CLARITIN®, Schering), promethazine hydrochloride (PHENERGAN®, Wyeth-Ayerst), pyrilamine, or anti-IgE (omalizumab; XOLAIR®; Genentech/Novartis).

In one embodiment according to this and all other aspects of the invention the polymer is a polysaccharide. In one embodiment according to this and according to all aspects of the invention the polymer is a bacterial capsular polysaccharide.

In one embodiment according to this and all other aspects of the invention the polymer is PSA1.

In one embodiment according to this and all other aspects of the invention the polymer is PSA2.

In one embodiment according to this and all other aspects of the invention the polymer is PSB.

In one embodiment according to this and all other aspects of the invention the polymer is *Streptococcus pneumoniae* capsular polysaccharide 1 (CP1).

In one embodiment according to this and all other aspects of the invention the polymer is de-N-acetylated *Salmonella typhi* Vi antigen.

In one embodiment according to this and all other aspects of the invention the polymer is aminated pectin (i.e., aminated polygalacturonic acid).

In one embodiment according to this and all other aspects of the invention the polymer is a synthetic peptidoglycan known as Compound 15 (described in published international patent application WO 03/075953).

In one embodiment according to this and all aspects of the invention the polymer is a polymer other than CP1 or synthetic peptidoglycan Compound 15.

In one embodiment according to this and all other aspects of the invention the polymer is a peptide. In one embodiment the peptide has a molecular weight of about 1.2 kDa-50 kDa.

In one embodiment according to this and all other aspects of the invention the polymer is $(K-D)_n$, wherein K is lysine, D is aspartic acid, and n is an integer between 10 and 100, inclusive. In one embodiment according to this and all other aspects of the invention the polymer is $[K-(Xaa)_m-D]_n$, wherein K is lysine, each Xaa is independently any neutral amino acid, m is an integer between 0 and 8, inclusive, D is aspartic acid, and n is an integer between 1 and 100, inclusive.

In one embodiment according to this aspect of the invention the administering involves administering multiple doses of the isolated polymer.

In one aspect the invention provides a method for treating a subject having an allergic condition associated with an identified allergen. The method according to this aspect of the invention includes the steps of (a) exposing a subject having an allergic condition associated with an identified allergen to the allergen, and (b) administering to the subject an isolated polymer in an effective amount to treat the allergic condition, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In various embodiments according to this aspect of the invention the exposing precedes, follows, or is substantially contemporaneous with the administering.

In one aspect the invention provides a method for treating asthma in a subject. The method according to this aspect involves administering to a subject having asthma an isolated polymer in an effective amount to treat the asthma, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In one embodiment according to this aspect of the invention the motif is a positively charged free amino moiety and a negatively charged moiety selected from the group consisting of phosphate, phosphonate, sulfate and sulfonate.

In one embodiment according to this aspect of the invention the polymer is a polymer other than CP1 or synthetic peptidoglycan Compound 15.

In one embodiment according to this aspect of the invention the subject is free of symptoms otherwise calling for treatment with the polymer.

In one embodiment according to this aspect of the invention the administering involves delivering an aerosol of the polymer to an airway of the subject.

In one embodiment according to this aspect of the invention the method further involves administering to the subject an anti-asthma medicament selected from the group consisting of glucocorticoids, beta adrenergic agonists, methylxanthines, anticholinergics, cromolyn, nedocromil, antihistamines, and anti-IgE. In various embodiments the anti-asthma medicament is beclomethasone dipropionate (VANCERIL®, Schering), flunisolide (AEROBID®, Forest), fluticasone propionate (FLOVENT®, GlaxoSmithKline), prednisone, methylprednisolone, triamcinolone acetonide (AZMACORT®, Aventis), albuterol sulfate (VENTOLIN®, GlaxoSmithKline; PROVENTIL®, Schering), epinephrine, isoproterenol hydrochloride, metaproterenol sulfate (ALUPENT®, Boehringer Ingelheim), terbutaline (BRETHINE®, LAMISIL®, Novartis), ipratropium bromide (ATROVENT®, Boehringer Ingelheim), theophylline, cromolyn, nedocromil, or anti-IgE (omalizumab; XOLAIR®; Genentech/Novartis).

In one embodiment according to this aspect of the invention the administering involves administering multiple doses of the isolated polymer.

In one aspect the invention provides a method for treating a subject having asthma associated with an identified allergen. The method according to this aspect of the invention includes the steps of (a) exposing a subject having asthma associated with an identified allergen to the allergen and (b) administering to the subject a polymer in an effective amount to treat the asthma, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In various embodiments according to this aspect of the invention the exposing precedes, follows, or is substantially contemporaneous with the administering.

In one aspect the invention provides a method for inducing interleukin 10 (IL-10) production. The method according to this aspect of the invention includes the steps of isolating a T regulatory cell, and contacting the T regulatory cell with an effective amount of a polymer to induce production of IL-10 by the T regulatory cell, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In one aspect the invention also provides a method for inducing inducible costimulatory molecule (ICOS) on a CD4+ cell. The method according to this aspect of the invention includes the step of contacting a CD4+ cell with an effective amount of a polymer to induce expression of ICOS on the CD4+ cell, wherein the polymer includes repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate; and measuring an increased ICOS expression on the CD4+ cell, wherein ICOS expression on the CD4+ cell is increased when ICOS expression after the contacting exceeds ICOS expression before the contacting.

The invention in one aspect provides a method for inducing proliferation of T regulatory (Treg) cells. The method according to this aspect of the invention includes the steps of isolating a population of naïve T cells, and contacting the population of naïve T cells with an effective amount of an isolated polymer to induce proliferation of T regulatory cells, wherein the polymer includes repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate.

In one embodiment according to this aspect of the invention the method further includes the step of contacting the population of naïve T cells with an antigen.

In one embodiment according to this aspect of the invention the method further includes the step of contacting the naïve T cells with exogenously supplied interleukin-2 (IL-2), interleukin-15 (IL-15), or a combination thereof.

The invention in one aspect provides a method for inducing proliferation of T regulatory (Treg) cells. The method according to this aspect of the invention includes the steps of isolating a population of T regulatory cells, and contacting the population of T regulatory cells with an effective amount of an isolated polymer to induce proliferation of the T regulatory cells, wherein the polymer includes repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate.

In one embodiment according to this aspect of the invention the method further includes the step of contacting the population of T regulatory cells with an antigen.

In one embodiment according to this aspect of the invention the method further includes the step of contacting the T regulatory cells with exogenously supplied interleukin-2 (IL-2), interleukin-15 (IL-15), or a combination thereof.

The invention in one aspect provides a method for inhibiting an antigen-specific immune response in a subject, wherein the antigen-specific response is other than an allergic condition or asthma. The method according to this aspect of the invention includes the step of administering to a subject in need of inhibition of an antigen-specific response, other than an allergic condition or asthma, (a) an antigen and (b) an isolated polymer in an effective amount to inhibit in the subject an immune response to the antigen, wherein the polymer includes repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate.

In various embodiments according to this aspect of the invention the administering the antigen precedes, follows, or is substantially contemporaneous with the administering the polymer.

In one embodiment the administering the polymer involves administering multiple doses of the polymer.

In one aspect the invention provides a composition that includes a conjugate that includes an antigen and a polymer, wherein the polymer includes repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate.

In one aspect the invention provides a pharmaceutical composition. The pharmaceutical composition according to this aspect of the invention includes an aerosol formulation of a polymer of repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate.

In one embodiment the composition includes a therapeutically effective amount of the aerosol formulation for treatment of an allergic condition.

In one embodiment the composition includes a therapeutically effective amount of the aerosol formulation for treatment of allergic asthma.

In one embodiment the pharmaceutical composition further includes another agent useful in the treatment of an allergic condition. In various embodiments the other agent is an anti-allergy medicament selected from the group consisting of glucocorticoids, antihistamines, and anti-IgE.

In one embodiment the pharmaceutical composition further includes another agent another agent useful in the treatment of asthma. In various embodiments the other agent is an anti-asthma medicament selected from the group consisting of glucocorticoids, beta adrenergic agonists, methylxanthines, anticholinergics, cromolyn, nedocromil, antihistamines, IL-10, and anti-IgE.

In a further aspect the invention provides an aerosol delivery system including a container with an interior, an aerosol generator in fluid connection with the interior of the container, and a polymer of repeating units of a charge motif characteristic of B. fragilis polysaccharide A (PSA), the motif being a positively charged free amino moiety and a negatively charged moiety selected from the group consisting of carboxyl, phosphate, phosphonate, sulfate and sulfonate, disposed within the interior of the container. The aerosol delivery system can be made to deliver a single dose or a plurality of doses. In one embodiment the container is a metered dose inhaler. In one embodiment the container is a dry powder inhaler. In another embodiment the container is a nebulizer. In yet another embodiment the container is a spray dispenser for topical delivery to a nasal epithelium or other respiratory epithelium. In one embodiment the aerosol delivery system further includes another agent useful in the treatment of an allergic condition or asthma.

DETAILED DESCRIPTION OF THE INVENTION

Figure 1A:
FIG. 1A is a pair of photographs depicting reduction of post-surgical adhesion formation by zwitterionic polysaccharide CP1. The left and right panels correspond to saline and CP1 treatments, respectively.

The invention is useful generally whenever it is desirable to induce IL-10-producing, CD45RB$^{lo}$ Treg cells, either in vivo or in vitro. More specifically, the invention is useful whenever it is desirable to treat an allergic or asthmatic condition in a subject, including prophylactically.

It was previously discovered by the present inventors that certain naturally occurring zwitterionic polysaccharides, modified polysaccharides, and peptides, all characterized by the presence of a specific charge motif, can be used to stimulate T cells to produce IL-2 and IL-10, and to induce protection against numerous bacteria, abscess and adhesion formation. See U.S. Pat. Nos. 5,679,654 and 5,700,787, both issued to Tzianabos et al., and published international patent application WO 00/59515, the entire contents of all of which are incorporated herein by reference.

It has now been discovered according to the present invention that these same and related zwitterionic polymers induce CD4+ T cells to express ICOS and promote the establishment and proliferation of IL-10-secreting Treg cells. These Treg cells are important not only as producers of IL-10 but also as immunoregulatory cells that can participate in preventing and subduing an inflammatory response or condition, or an allergic response or condition in a subject. As one featured aspect of the invention, the zwitterionic polymers are discovered to be useful in the treatment and prevention of an allergic condition in a subject. As one featured aspect of the invention, the zwitterionic polymers are discovered to be useful in the treatment and prevention of asthma.

In one aspect of the invention, a method is provided for treating a subject having an allergic condition. The method according to this aspect involves administering to a subject having an allergic condition an isolated polymer in an effective amount to treat the allergic condition, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

The polymers useful according to this and all other aspects of the invention are described in detail further below. Briefly, they are zwitterionic polymers that include both polysaccharides (including PSA) as well as non-polysaccharide polymers. The polymers can be naturally occurring polymers, modified forms of naturally occurring polymers, or other polymers not found in nature.

An "allergic condition" or, equivalently, "allergy", as used herein refers to an acquired hypersensitivity to a substance (allergen). Allergic conditions include but are not limited to allergic asthma, hayfever (seasonal rhinitis), allergic rhinitis, allergic conjunctivitis, eczema, urticaria, food allergies, and other atopic conditions.

An "allergen" refers to a substance that can induce an allergic or asthmatic response in a susceptible subject. The list of allergens is enormous and can include pollens, insect venoms, animal dander, house dust mite, dust, fungal spores, latex, and drugs (e.g., penicillin). Examples of natural, animal and plant allergens include proteins specific to the following genera: *Canis* (*Canis familiaris*); *Dermatophagoides* (e.g., *Dermatophagoides farinae*); *Felis* (*Felis domesticus*); *Ambrosia* (*Ambrosia artemiisfolia*); *Lolium* (e.g., *Lolium perenne* or *Lolium multiflorum*); *Cryptomeria* (*Cryptomeria japonica*); *Alternaria* (*Alternaria alternata*); Alder; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g., *Plantago lanceolata*); *Parietaria* (e.g., *Parietaria officinalis* or *Parietaria judaica*); *Blattella* (e.g., *Blattella germanica*); *Apis* (e.g., *Apis multiflorum*); *Cupressus* (e.g., *Cupressus sempervirens*, *Cupressus arizonica* and *Cupressus macrocarpa*); *Juniperus* (e.g., *Juniperus sabinoides*, *Juniperus virginiana*, *Juniperus communis* and *Juniperus ashei*); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Festuca elatior*); *Poa* (e.g., *Poa pratensis* or *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*). Allergens also include peptides and polypeptides such as are used in experimental animal models of allergy and asthma, including ovalbumin (OVA) and *Schistosoma mansoni* egg antigen.

As used herein, a "subject" shall refer to a human or other mammal, including but not limited to mice, rats, rabbits, and non-human primates.

A "subject having an allergic condition" as used herein refers to a subject with an existing allergic condition or a known or suspected predisposition toward developing an allergic condition. Thus the subject can have an active allergic condition or a latent allergic condition. It is not necessary that the allergen be known. However, certain allergic conditions are associated with seasonal or geographical environmental factors, which may but need not be apparent to the subject. In one embodiment the allergic condition is intentionally induced in the subject for experimental purposes.

In one embodiment according to this aspect of the invention the subject is free of indications otherwise calling for treatment with the polymer. In this embodiment the subject does not have an infection, surgery, trauma, or other disease or risk factor associated with abscess or surgical adhesion formation; a Th1-cell-responsive disorder (insulin-dependent diabetes mellitus, experimental allergic encephalomyelitis (EAE), inflammatory bowel disease, and allograft rejection); a disorder characterized by an inappropriate IgG antibody response to specific antigen (acute glomerulonephritis, Goodpasture's syndrome, autoimmune arthritis including rheumatoid arthritis, systemic lupus erythematosus (SLE; lupus), AIDS, Sjögren's syndrome, autoimmune hemolytic anemia, idiopathic thrombocytopenic purpura (ITP), and certain forms of thyroiditis).

As a feature of the invention, the polymer can be administered repeatedly and/or chronically to a subject having an allergic condition to treat the allergic condition. As is described below, the repeated or chronic administration can take place over days, weeks, months, or even years. In one embodiment the polymer is administered repeatedly on a scheduled basis, e.g., daily or weekly. In one embodiment the polymer is administered repeatedly on a symptomatic basis.

In one aspect the invention provides a method for treating a subject having an allergic condition associated with an identified allergen. The method according to this aspect of the invention involves (a) exposing a subject having an allergic condition associated with an identified allergen to the allergen, and (b) administering to the subject an isolated polymer in an effective amount to treat the allergic condition, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate. The step of exposing the subject having the allergic condition associated with the identified allergen to the allergen can be active or passive. That is, actively exposing can involve deliberate administration of allergen to the subject; passively exposing can involve accidental or environmental contact of the subject with the allergen. In a specific embodiment the exposing step specifically involves administering the known allergen to the subject, in an amount effective to induce in the subject an allergic response to the allergen in absence of the administration of the polymer.

In various embodiments the step of exposing the subject to the allergen can precede, follow, or be contemporaneous with the step of administering to the subject the polymer in the effective amount to treat the allergic condition. In addition, the route of exposing and the route of administration can be the same or they can be different.

The invention in one aspect provides the use of a zwitterionic polymer in the manufacture of a medicament for use in the treatment of an allergic condition. The zwitterionic polymer is as described elsewhere herein, and the use involves placing an effective amount of the polymer, or a hydrate or pharmaceutically acceptable salt thereof, in a pharmaceutically acceptable carrier, for use in the treatment of an allergic condition of a subject. The use may involve the manufacture of unit doses of the polymer suitable for use in the treatment of the allergic condition. The allergic condition can be any allergic condition, including, without limitation, any allergic or atopic condition listed above.

The invention in one aspect provides a method for treating asthma in a subject. The method according to this aspect involves administering to a subject having asthma an isolated polymer in an effective amount to treat the asthma, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In one embodiment the motif is a positively charged free amino moiety and a negatively charged moiety selected from the group consisting of phosphate, phosphonate, sulfate and sulfonate.

In one embodiment the polymer is a polymer other than CP1 or synthetic peptidoglycan Compound 15, described below.

As used herein, "asthma" refers to a disorder of the respiratory system that is episodic and characterized by inflammation with narrowing of the airways and increased reactivity of the airways to inhaled agents. Asthma is frequently, although not exclusively associated with atopic or allergic symptoms. Symptoms of asthma are widely recognized to include dyspnea, cough, and wheezing; while all three symptoms typically coexist, their coexistence is not required to make a diagnosis of asthma.

A "subject having asthma" as used herein refers to a subject with an existing acute exacerbation of asthma, either new-onset or recurrent, or a history of asthma, or a known or suspected predisposition toward developing asthma. A subject having asthma thus can have active asthma or can be asymptomatic and between acute exacerbations. In one embodiment a subject having asthma is a subject having asthma that is associated with allergic symptoms, i.e., allergic asthma.

In one embodiment according to this aspect of the invention the subject is free of symptoms otherwise calling for treatment with the polymer, as described above.

In one embodiment according to this aspect of the invention the administering involves delivering an aerosol of the polymer to an airway of the subject. The zwitterionic polymer in this embodiment is administered to an airway of the subject in order to treat an asthmatic condition in the subject. As used herein, an "airway of the subject" refers to any suitable conducting or gas-exchanging surface of the respiratory system of the subject. Such airways typically include but are not limited to the trachea, bronchi, bronchioles, and terminal and respiratory bronchioles. In one embodiment the airway is nasal epithelium. Delivery of an aerosol of the polymer to an airway typically involves inhalation of the aerosol. The inhalation can be passive or it can be assisted by a pressurized aerosol delivery system or device. Administration of therapeutic agents, including the polymers of the invention, to airways can conveniently be accomplished by using an aerosol or spray device or delivery system. Examples of such aerosol and spray delivery systems and devices are well known in the art and include metered dose inhalers, dry powder inhalers, ultrasonic nebulizers, other liquid nebulizers, nasal sprays, and the like.

The polymers of the invention can also be formulated as nose drops for administration to nasal epithelium, for use in the treatment of allergy or asthma.

As a feature of the invention, the polymer can be administered repeatedly and/or chronically to a subject having asthma to treat the asthma. As is described below, the repeated or chronic administration can take place over days, weeks, months, or even years. In one embodiment the polymer is administered repeatedly on a scheduled basis, e.g., daily or weekly. In one embodiment the polymer is administered repeatedly on a symptomatic basis.

In one aspect the invention provides a method for treating a subject having asthma associated with an identified allergen. The method according to this aspect of the invention involves (a) exposing a subject having asthma associated with an identified allergen to the allergen, and (b) administering to the subject a polymer in an effective amount to treat the asthma, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate. The step of exposing the subject having asthma associated with the identified allergen to the allergen can be active or passive. That is, actively exposing can involve deliberate administration of allergen to the subject; passively exposing can involve accidental or environmental contact of the subject with the allergen. In a specific embodiment the exposing step specifically involves administering the known allergen to the subject, in an amount effective to induce an acute exacerbation of asthma in the subject in absence of the administration of the polymer.

In various embodiments the step of exposing the subject to the allergen can precede, follow, or be contemporaneous with the step of administering to the subject the polymer in the effective amount to treat the asthma. In addition, the route of exposing and the route of administration can be the same or they can be different.

The invention in one aspect provides the use of a zwitterionic polymer in the manufacture of a medicament for use in the treatment of asthma. The zwitterionic polymer is as described elsewhere herein, and the use involves placing an effective amount of the polymer, or a hydrate or pharmaceutically acceptable salt thereof, in a pharmaceutically acceptable carrier, for use in the treatment of asthma in a subject. The use may involve the manufacture of unit doses of the polymer suitable for use in the treatment of the asthma. In one embodiment the asthma is allergic asthma.

Certain aspects of the invention involve the administration of an effective amount of the polymer to a subject, either to treat an allergic condition or to treat asthma. An "effective amount" as used herein refers in general to an amount of a composition that, alone or together with further doses, stimulates a desired response. With respect to a composition of the invention, an "effective amount" as used herein refers to an amount of a preparation of the invention that, alone or together with further doses, stimulates a desired response. Thus an effective amount can but need not be provided in a single administration. Also as used herein, an "effective amount to treat" a condition refers to an amount that is sufficient to prevent the onset of, slow the progression of, ameliorate, or eliminate a condition or side effect associated with a condition in a subject. A therapeutically effective amount, with respect to a condition being treated, refers to an effective amount to treat the condition.

Thus an effective amount to treat an allergic condition in a subject is an amount that is sufficient to prevent the onset of, slow the progression of, ameliorate, or eliminate the allergic condition or a side effect associated with the allergic condition in the subject. In like manner, an effective amount to treat asthma in a subject is an amount that is sufficient to prevent the onset of, slow the progression of, ameliorate, or eliminate asthma or a side effect associated with asthma in the subject. Those of skill in the art will recognize how to assess the effectiveness of a treatment designed to prevent or alleviate an allergic condition or asthma in a subject, using accepted clinical skills and laboratory measurements.

For example, allergic conditions and asthma are associated with IgE. Thus in addition to monitoring well known clinical signs and symptoms of allergy and asthma, a clinician can measure serum IgE in a subject to be treated according to a method of the invention. A decrease in serum IgE is expected to provide an objective measure of the efficacy of treatment. Although less convenient than serum, IgE can be measured in bronchoalveolar lavage (BAL) fluid.

In certain embodiments according to the foregoing aspects of the invention, the polymer is administered in conjunction with administering another agent that is useful for treating the allergic condition or asthma. The other agent useful for treating the allergic condition or asthma can be administered before, after, or simultaneously with the administering of the polymer. In addition, the polymer and the other agent can be administered by the same route or by different routes. Thus the invention embraces the use of different agents on the same or on different schedules where the polymer and the other agent useful for treating the allergic condition or asthma are to be administered on a repeated basis. The other agent useful for treating the allergic condition or asthma can be administered in an amount that, alone, is effective for treating the allergic condition or asthma, or it can be administered in a lesser amount. In one embodiment the polymer and the other agent useful for treating the allergic condition or asthma are presented in a single pharmaceutical composition containing both the polymer and the other agent. Thus "cocktails" including the polymers and the other agent or agents useful for treating the allergic condition or asthma are contemplated.

Agents useful for treating an allergic condition include but are not limited to glucocorticoids, e.g., prednisone and methylprednisolone; antihistamines, particularly the $H_1$-receptor blocking antihistamines, e.g., chlorcyclizine, chlorpheniramine; diphenhydramine hydrochloride (BENADRYL®, Parke-Davis), fexofenadine hydrochloride (ALLEGRA®, Aventis), hydroxyzine hydrochloride (ATARAX®, Pfizer), loratadine (CLARITIN®, Schering), promethazine hydrochloride (PHENERGAN®, Wyeth-Ayerst), and pyrilamine; and anti-IgE (omalizumab; XOLAIR®; Genentech/Novartis).

Agents useful for treating asthma include but are not limited to glucocorticoids, e.g., beclomethasone dipropionate (VANCERIL®, Schering), flunisolide (AEROBID®, Forest), fluticasone propionate (FLOVENT®, GlaxoSmithKline), prednisone, methylprednisolone, and triamcinolone acetonide (AZMACORT®, Aventis); antihistamines, listed above; beta adrenergic agonists, e.g., albuterol sulfate (VENTOLIN®, GlaxoSmithKline; PROVENTIL®, Schering), epinephrine, isoproterenol hydrochloride, metaproterenol sulfate (ALUPENT®, Boehringer Ingelheim), and terbutaline (BRETHINE®, LAMISIL®, Novartis); anticholinergics, e.g., ipratropium bromide (ATROVENT®, Boehringer Ingelheim); methylxanthines, e.g., theophylline; cromolyn; nedocromil; and anti-IgE (omalizumab; XOLAIR®; Genentech/Novartis). IL-10 itself may be useful as another agent to treat asthma.

Other immunomodulators such as cytokines can be delivered in conjunction with the polymers of the invention, and "cocktails" including the polymers and the cytokines are contemplated. The cytokines contemplated are those that will enhance the beneficial effects that result from administering the polymers according to the invention. Cytokines are factors that support the growth and maturation of cells, including lymphocytes. The cytokines can act directly on T cells or indirectly on T cells through other cells. It is believed that the addition of cytokines will augment cytokine activity stimulated in vivo by carrying out the methods of the invention. One such cytokine is IL-10. Other cytokines of particular interest in this regard are IL-2 and IL-15. Additional cytokines include, without limitation, IL-1, IL-3, IL-4, IL-5, IL-6, IL-7, IL-12, IL-13, IL-17, IL-18, IL-19, IFN-α, IFN-β, IFN-γ, TNF-α, TGF-β, G-CSF, M-CSF, GM-CSF, and lymphotoxin.

In one aspect the invention provides a method for inducing interleukin 10 (IL-10) production. The method according to this aspect of the invention involves isolating a T regulatory cell, and contacting the T regulatory cell with an effective amount of a polymer to induce production of IL-10 by the T regulatory cell, wherein the polymer includes repeating units of a charge motif characteristic of $B.$ $fragilis$ polysaccharide A (PSA), the motif being a positively charged free amino moiety and a negatively charged moiety selected from the group consisting of carboxyl, phosphate, phosphonate, sulfate and sulfonate.

As used herein, a "T regulatory cell" or, equivalently, "Treg cell" refers to a type of $CD4^+$ T lymphocyte that secretes large amounts of IL-10 but only small amounts, if any, of IL-4 and IL-13. Akbari O et al. (2002) $Nat$ $Med$ 8:1024-32. Treg cells are to be distinguished from both Th2 and Th1 $CD4^+$ T cells, even though all three types of T cells have been reported to secrete IL-10. As disclosed herein, Treg cells are further characterized by their expression of ICOS and their limited expression of CD45RB)(CD45RB$^{lo}$. Treg cells are believed to play an important role in peripheral tolerance. These cells, sometimes referred to as regulatory or suppressor T cells, act as powerful inhibitors of antigen-specific T-cell activation.

There is now reported to be more than a single type of T regulatory cell. For recent reviews, see Jonuleit H et al. (2003) $J$ $Immunol$ 171:6323-7, and Shevach E M (2002) $Nat$ $Immunol$ 2:389-400. One type of Treg cell is the naturally occurring $CD4^+CD25^+$ Treg cell, which develops directly from $CD4^+$ T cell precursors during positive selection in the thymus, under the influence of medium avidity interactions with thymic epithelial cells. These cells are reported to represent 5-10 percent of all peripheral $CD4^+$ T cells. Mice, thymectomized by day 3 after birth, lack this population of cells and characteristically develop various autoimmune diseases. Sufi-Payer E et al. (1998) $J$ $Immunol$ 160:1212-8. Freshly isolated $CD4^+CD25^+$ Treg cells are reported to be hyporesponsive to allogeneic or polyclonal activation in vitro. However, they have been reported to suppress proliferation of conventional $CD4^+CD25^-$ T cells in coculture, and suppression occurs only when the $CD4^+CD25^+$ Treg cells are activated through their T-cell antigen receptor. Naturally occurring $CD4^+CD25^+$ Treg cells are reported to exert their suppressive effects on CD25 T cells, at least in vitro, via a strictly cell contact-dependent manner, independent of soluble suppressive cytokines, the mechanism of which has yet to be fully elucidated. Jonuleit H et al. (2003) $J$ $Immunol$ 171:6323-7.

A second type of Treg cell is the induced $CD4^+$ Treg cell. These Treg cells, in contrast to naturally occurring $CD4^+CD25^+$ Treg cells, exert their suppressive effects in a cell contact-independent manner that involves secretion of soluble suppressive cytokines, including IL-10 and TGF-β. These cells are secondary suppressor T cells and they develop in the periphery, rather than in the thymus. Induced CD4+ Treg cells are believed to include at least two subtypes, Tr1 cells which produce large amounts of IL-10 but only modest amounts of TGF-β, and Th3 cells which produce mostly TGF-β. Tr1 cells are also referred to in the literature as type 1 T-regulatory cells and as IL-10-producing Treg cells. It has now been discovered as part of the instant invention, that these Treg cells, which are distinct from $CD4^+CD25^+$ Treg cells, express ICOS and are CD45RB$^{lo}$. These Treg cells can be induced from naïve T cells upon repeated antigen exposure or antigen stimulation. Groux H et al. (1997) $Nature$ 389:737-42. Alternatively, IL-10-secreting Treg cells have been generated in vitro by culturing T cells in the presence of large amounts of exogenous IL-10, with immature dendritic cells (DC), or certain immunosuppressive drugs, including a combination of 1,25(OH)$_2$-vitamin D3 and dexamethasone. Groux H et al. (1997) $Nature$ 389:737-42; Jonuleit H et al. (2001) $J$ $Exp$ $Med$ 193:1285-94; Barrat F J et al. (2002) $J$ $Exp$ $Med$ 195:603-16. Each of these in vitro methods may be of limited value for use in vivo, owing to unwanted side effects and technical demands. Supernatants of activated Tr1 cells strongly reduce the capacity of dendritic cells to induct alloantigen-specific proliferation. Groux H (2003) $Transplantation$ 75:8S-12S. Furthermore, supernatants of activated human Tr1 cells have been reported to promote the differentiation of naïve $CD4^+$ T cells into Tr1 cells in vitro, in an IL-10-dependent manner. Roncarolo M G et al. (2001) $Immunol$ $Rev$ 182:68-79.

Interleukin-10 (IL-10) is a pleiotropic cytokine that has antiinflammatory properties through its ability to downregulate antigen presentation and macrophage activation. It also plays a role in B-cell activation and autoantibody production. The IL-10 family of cytokines includes IL-19, IL-20, MDA7, and IL-22. As originally described, IL-10 is produced by B cells, T helper cells, and cells of the monocyte/macrophage lineage. Tan J C et al. (1993) $J$ $Biol$ $Chem$ 268: 21053-9. Akbari O et al. (2003) $Nature$ $Med$ 8: 1024-32 noted that Th1 cells secreting IFN-γ regulate Th2 cells and may be involved in downregulating Th2-driven airway hyperreactivity and asthma. However, IFN-γ may also contribute to the severity of disease by exacerbating pulmonary inflammation. Surprisingly, after exposure of mice to allergen by the respiratory route, Treg cells developed, producing high levels of IL-10, typically considered a Th2 cytokine. The Treg cells downmodulated allergen-induced airway hyperreactivity in previously sensitized mice. Akbari O et al. (2003) $Nature$ $Med$ 8: 1024-32 suggested that IL-10 may initially be involved in the polarization of Th2 responses but plays a regulatory role late in immune responses to attenuate Th2-driven inflammatory activity.

Production of IL-10 can be measured using any method suitable for quantitating the amount of IL-10 messenger RNA or IL-10 polypeptide present in a sample. The amount of IL-10 mRNA can be measured, for example, by reverse transcriptase-polymerase chain reaction (RT-PCR) using suitable oligonucleotide primers and techniques familiar to those of skill in the art. In one embodiment the amount of IL-10 polypeptide expressed within a cell can be measured using flow cytometry techniques. Flow cytometry will involve the use of an antibody that binds specifically to IL-10 and optionally includes a fluorescent tag. Monoclonal anti-IL-10 antibodies are available from commercial suppliers. In another embodiment the amount of IL-10 polypeptide expressed by a cell can be assessed using an enzyme-linked immunofluorescence assay (ELISA), reagents and kits for which are available from commercial suppliers. In yet another embodiment the amount of IL-10 polypeptide expressed by a cell can be assessed using a biological assay that is based, either directly or indirectly, on IL-10 interacting with its receptor. The biological assay can be an in vitro assay or it can be an in vivo assay.

In one aspect the invention also provides a method for inducing expression of inducible costimulatory molecule (ICOS) on a CD4+ cell. The method according to this aspect of the invention involves contacting a CD4+ cell with an effective amount of an isolated polymer to induce expression of ICOS on the CD4+ cell, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate; and measuring an increased ICOS expression on the CD4+ cell, wherein ICOS expression on the CD4+ cell is increased when ICOS expression after the contacting exceeds ICOS expression before the contacting.

ICOS is a recently described inducible costimulatory molecule related to CD28 that is expressed on T cells. Hutloff A et al. (1999) *Nature* 397:263-6. The cognate ligand for ICOS, ICOSL, is expressed on the surface of antigen-presenting cells (APC). ICOS-ICOSL interactions give rise to induction of IL-10 secretion by T cells. Sharpe A H et al. (2002) *Nat Rev Immunol* 2:116-26. Nucleotide and amino acid sequences of human ICOS are known and publicly available from GenBank under accession numbers NM_012092 and AJ277832; NP_036224 and CAC06612, respectively.

ICOS expression can be measured using any method suitable for quantitating the amount of ICOS messenger RNA or ICOS polypeptide present in a sample. The amount of mRNA can be measured, for example, by reverse transcriptase-polymerase chain reaction (RT-PCR) using suitable oligonucleotide primers and techniques familiar to those of skill in the art. In one embodiment the amount of ICOS polypeptide expressed by a cell can be measured using flow cytometry techniques. In another embodiment the amount of ICOS polypeptide expressed by a cell can be assessed using fluorescence microscopy. Both flow cytometry and fluorescence microscopy involve the use of antibodies that bind specifically to ICOS and that optionally include a fluorescent tag. Monoclonal anti-ICOS antibodies are available from commercial suppliers. In another embodiment the amount of ICOS polypeptide expressed by a cell can be assessed using a biological assay that is based, either directly or indirectly, on ICOS-ICOSL interaction. The biological assay can be an in vitro assay or it can be an in vivo assay. Examples of such assays are provided in the Examples section below.

The invention in one aspect provides a method for inducing proliferation of T regulatory cells. The method according to this aspect of the invention involves isolating a population of naïve T cells, and contacting the population of naïve T cells with an effective amount of an isolated polymer to induce proliferation of T regulatory cells, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate. As used herein, isolating a population of T cells refers generally to isolating a population of T cells from whole blood, spleen, or any other source of lymphocytes, such that at least 80 percent of the isolated population of cells are T cells. In one embodiment T cells represent at least 90 percent of the isolated population of cells. In one embodiment T cells represent at least 95 percent of the isolated population of cells. In one embodiment T cells represent at least 98 percent of the isolated population of cells. Methods for isolating T cells from a mixed population of blood cells or splenocytes are well known in the art and include, for example, cell sorting and density gradient centrifugation in combination with positive or negative selection on nylon wool. The method according to this aspect of the invention can optionally include the step of isolating the resulting Treg cells from other cells, following the contacting step. As in other aspects of the invention, a polymer useful according to this aspect of the invention can be any one or combination of the zwitterionic polymers described in further detail below.

In one embodiment according to this aspect of the invention the method further entails contacting the population of naïve T cells with an antigen, for example, continuously throughout the time the cells are contacted with the zwitterionic polymer.

In one embodiment according to this aspect of the invention the method further entails contacting the population of naïve T cells with exogenously supplied cytokine that is effective to support or stimulate proliferation of Treg cells. In one embodiment the method further entails contacting the population of naïve T cells with exogenously supplied IL-2, IL-15, or a combination of IL-2 and IL-15. These cytokines can be obtained as purified recombinant proteins from various commercial suppliers. They may be supplied as Fc fusion proteins or other stabilized forms, e.g., PEGylated IL-2 or IL-15, all of which are known in the art.

In one embodiment according to this aspect of the invention the step of isolating a population of naïve T cells involves isolating a population of naïve T cells that is essentially free of naturally occurring $CD4^+CD25^+$ Treg cells. This can be accomplished through positive or negative selection, for example, using standard fluorescence-activated cell sorting (FACS) techniques, gating on CD4 and CD25, or using magnetic beads coated with CD4 and CD25. The method according to this embodiment thus entails inducing a population of IL-10-producing $CD4^+$ Treg cells in the absence of contact with $CD4^+CD25^+$ Treg cells. The method according to this embodiment can entail inducing a population of induced $CD4^+$ Treg cells without the influence of another agent previously described to be useful in methods for inducing such cells, viz., large amounts of exogenous IL-10, with immature dendritic cells (DC), or certain immunosuppressive drugs, including a combination of $1,25(OH)_2$-vitamin D3 and dexamethasone. Groux H et al. (1997) *Nature* 389:737-42;

Jonuleit H et al. (2001) *J Exp Med* 193:1285-94; Banat F J et al. (2002) *J Exp Med* 195:603-16.

In an alternative method, a general population of cells that includes naïve T cells is contacted with an effective amount of an isolated polymer, described herein, to induce proliferation of T regulatory cells, and then proliferated T regulatory cells are isolated from the general population of cells.

The invention in one aspect provides a method for inducing proliferation of T regulatory cells. The method according to this aspect of the invention involves isolating a population of T regulatory cells, and contacting the population of T regulatory cells with an effective amount of a polymer to induce proliferation of the T regulatory cells, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate. The method according to this aspect of the invention can optionally include the step of isolating the resulting Treg cells from other cells, following the contacting step. As in other aspects of the invention, a polymer useful according to this aspect of the invention can be any one or combination of the zwitterionic polymers described in further detail below.

In one embodiment according to this aspect of the invention the method further entails contacting the population of T regulatory cells with an antigen, for example, continuously throughout the time the cells are contacted with the zwitterionic polymer.

In one embodiment according to this aspect of the invention the method further entails contacting the population of T regulatory cells with exogenously supplied cytokine that is effective to support or stimulate proliferation of Treg cells. In one embodiment the method further entails contacting the population of T regulatory cells with exogenously supplied IL-2, IL-15, or a combination of IL-2 and IL-15. These cytokines, or their corresponding Fc fusion proteins or other stabilized forms, are formulated and available as described above.

In one embodiment according to this aspect of the invention the step of isolating a population of T regulatory cells involves isolating a population of T regulatory cells that is essentially free of naturally occurring $CD4^+CD25^+$ Treg cells. The method according to this embodiment thus entails inducing a population of IL-10-producing $CD4^+$ Treg cells in the absence of contact with $CD4^+CD25^+$ Treg cells. The method according to this embodiment also can entail inducing a population of induced $CD4^+$ Treg cells without the influence of another agent previously described to be useful in methods for inducing such cells, viz., large amounts of exogenous IL-10, with immature dendritic cells (DC), or certain immunosuppressive drugs, including a combination of 1,25 $(OH)_2$-vitamin D3 and dexamethasone. Groux H et al. (1997) *Nature* 389:737-42; Jonuleit H et al. (2001) *J Exp Med* 193: 1285-94; Barrat F J et al. (2002) *J Exp Med* 195:603-16.

In an alternative method, a general population of cells that includes T regulatory cells is contacted with an effective amount of an isolated polymer, described herein, to induce proliferation of T regulatory cells, and then proliferated T regulatory cells are isolated from the general population of cells.

An expanded population of Treg cells induced according to a method of the invention can be administered to a subject in need of downregulation of an immune response. For example, an expanded population of Treg cells (typically derived from the subject to be treated) induced according to a method of the invention can be administered to a subject having an allergic condition or to a subject having asthma, as described herein, to treat the allergic condition or asthma. In the case of a subject having an allergic condition or response, the administering of the Treg cells can take place prior to, essentially concurrent with, or following exposure of the subject to an allergen that is associated with the allergic condition or response in the subject. The exposure of the subject to the allergen can be passive, e.g., through accidental environmental contact with the allergen, or it can be active, e.g., through deliberate administration of the allergen to the subject, e.g., by injection or aerosol administration. In the case of a subject with asthma, the administering can take place prior to, essentially concurrent with, or following the onset of an acute exacerbation of asthma. In addition, in the case of a subject with allergic asthma, the administering of the Treg cells can take place prior to, essentially concurrent with, or following exposure of the subject to an allergen that is associated with the allergic asthma in the subject. The exposure to the allergen can be passive or it can be active, as described above.

As used herein, a subject in need of downregulation of an immune response includes, without limitation, subjects having a condition or disease chosen from abscesses, post-surgical adhesions, sepsis, rheumatoid arthritis, myasthenia gravis, inflammatory bowel disease, colitis, systemic lupus erythematosus, multiple sclerosis, coronary artery disease, diabetes, hepatic fibrosis, psoriasis, eczema, acute respiratory distress syndrome, acute inflammatory pancreatitis, endoscopic retrograde cholangiopancreatography-induced pancreatitis, burns, atherogenesis of coronary, cerebral, and peripheral arteries, appendicitis, cholecystitis, diverticulitis, visceral fibrotic disorders, wound healing, skin scarring disorders, granulomatous disorders, asthma, pyoderma gangrenosum, Sweet's syndrome, Behçet's syndrome, primary sclerosing cholangitis, and cell, tissue, or organ transplantation.

In one embodiment naïve T cells are isolated from a subject in need of downregulation of an immune response, then contacted with an effective amount of polymer as described herein to induce proliferation of Treg cells, and then an effective amount of the resulting unsorted population of cells is administered to the subject to downregulate the immune response in the subject. In another embodiment naïve T cells are isolated from a subject in need of downregulation of an immune response, then contacted with an effective amount of polymer as described herein to induce proliferation of Treg cells, resulting Treg cells are isolated from the treated cells, and then an effective amount of the isolated population of Treg cells is administered to the subject to downregulate the immune response in the subject.

In one embodiment Treg cells are isolated from a subject in need of downregulation of an immune response, then contacted with an effective amount of polymer as described herein to induce proliferation of the Treg cells, and then an effective amount of the resulting expanded population of Treg cells is administered to the subject to downregulate the immune response in the subject.

In one embodiment the polymer is a polymer other than CP1 or synthetic peptidoglycan Compound 15.

The proliferation of T cells in general can be measured using any method suitable for quantitating the number of T cells present in a sample. T cells can be isolated, if necessary, and the number of T cells can be measured, for example, by measuring $^3[H]$-thymidine incorporation, flow cytometry, and other techniques familiar to those of skill in the art. These methods can be adapted for the purpose of measuring the proliferation of Treg cells. For example, as disclosed herein, the Treg cells are $CD4^+$, $ICOS^+$, $CD45RB^{lo}$, and stain positive for intracellular IL-10.

The invention in one aspect provides a method for inhibiting an antigen-specific immune response in a subject, wherein the antigen-specific response is other than an allergic condition or asthma. The method according to this aspect of the invention involves the step of administering to a subject in need of inhibition of an antigen-specific response, other than an allergic condition or asthma, (a) an antigen and (b) a polymer in an effective amount to inhibit in the subject an immune response to the antigen, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In various embodiments the administering of the antigen can precede, follow, or be contemporaneous with the administering of the polymer. In addition, the site of administration of the antigen and the site of administration of the polymer can be the same or they can be different. Further still, the mode of administration of the antigen and the mode of administration of the polymer can be the same or they can be different.

As a feature of the invention, the polymer, in this case in conjunction with administration of the antigen, can be administered repeatedly and/or chronically to inhibit in the subject the immune response to the antigen. As is described below, the repeated or chronic administration can take place over days, weeks, months, or even years. In one embodiment the polymer is administered repeatedly on a scheduled basis, e.g., daily or weekly. In one embodiment the polymer is administered repeatedly on a symptomatic basis.

In one embodiment the antigen is present as a conjugate with the polymer. A conjugate, as used herein, refers to any combination of two or more different compositions in which the different compositions are physically or chemically linked to one another, either directly or indirectly. In one embodiment the different compositions, e.g., the antigen and the polymer, are chemically linked together by a covalent bond. Where the linkage is indirect, there may be a linker moiety interposed between or otherwise connecting the two different compositions. Methods for making covalent linkages between polysaccharides and peptides (or polypeptides) are well known in the art, as are methods for covalently linking peptides to peptides.

In one embodiment according to this aspect of the invention the subject is free of indications otherwise calling for treatment with the polymer. In this embodiment the subject does not have an infection, surgery, trauma, or other disease or risk factor associated with abscess or surgical adhesion formation; a Th1-cell-responsive disorder (insulin-dependent diabetes mellitus, experimental allergic encephalomyelitis (EAE), inflammatory bowel disease, and allograft rejection); a disorder characterized by an inappropriate IgG antibody response to specific antigen (acute glomerulonephritis, Goodpasture's syndrome, autoimmune arthritis including rheumatoid arthritis, systemic lupus erythematosus (SLE; lupus), AIDS, Sjögren's syndrome, autoimmune hemolytic anemia, idiopathic thrombocytopenic purpura (ITP), and certain forms of thyroiditis).

In one aspect the invention provides a novel composition. The composition according to this aspect of the invention includes a conjugate of an antigen and a polymer, wherein the polymer includes repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate. The antigen and the polymer of the conjugate composition are physically or chemically associated, either directly or indirectly. In one embodiment the antigen and the polymer are chemically associated through a covalent bond. In one embodiment the antigen and the polymer are chemically associated through a linker moiety connecting the two. In one embodiment the antigen and the polymer are associated physically with or within a liposome or other similar delivery vehicle.

An antigen typically is any substance that can be specifically bound by a T-cell antigen receptor, antibody, or B-cell antigen receptor. Antigenic substances include, without limitation, peptides, proteins, carbohydrates, lipids, phospholipids, nucleic acids, autacoids, and hormones. Antigenic substances further specifically include antigens that are classified as allergens, cancer antigens, and microbial antigens. Antigens also include autoantigens.

The antigen can be an antigen that is or is derived from an infectious microbial agent, including a bacterium, a virus, a fungus, or a parasite. Examples of infectious bacteria include: *Helicobacter pyloris, Borrelia burgdorferi, Legionella pneumophilia, Mycobacteria* sps (such as. *M. tuberculosis, M. avium, M. intracellulare, M. kansasii*, and *M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, and *Actinomyces israelii*.

Examples of infectious viruses include: Retroviridae (including but not limited to human immunodeficiency virus (HIV)); Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bunyaviridae (for example, Hantaan viruses, bunya viruses, phleboviruses, and Nairo viruses); Arena viridae (hemorrhagic fever viruses); Reoviridae (e.g., reoviruses, orbiviurses, and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious fungi include, but are not limited to, *Cryptococcus neoformans, Histoplasma capsulatum, Coccidioides immitis, Blastomyces dermatitidis, Chlamydia trachomatis,* and *Candida albicans.*

The antigen can be a cancer antigen. A cancer antigen as used herein is a compound, such as a peptide or protein, associated with a tumor or cancer cell surface and which is capable of provoking an immune response when expressed on the surface of an antigen-presenting cell in the context of a major histocompatibility complex (MHC) molecule. Cancer antigens can be prepared from cancer cells either by preparing crude extracts of cancer cells, for example, as described in Cohen P A et al. (1994) *Cancer Res* 54:1055-8, by partially purifying the antigens, by recombinant technology, or by de novo synthesis of known antigens. Cancer antigens include but are not limited to antigens that are recombinantly expressed, an immunogenic portion thereof, or a whole tumor or cancer cell. Such antigens can be isolated or prepared recombinantly or by any other means known in the art.

Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, cdc27, adenomatous polyposis *coli* protein (APC), fodrin, Connexin 37, Ig-idiotype, p15, gp75, GM2 and GD2 gangliosides, viral products such as human papillomavirus proteins, Smad family of tumor antigens, lmp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

Cancers or tumors and tumor antigens associated with such tumors (but not exclusively), include acute lymphoblastic leukemia (etv6; aml1; cyclophilin b), B cell lymphoma (Ig-idiotype), glioma (E-cadherin; α-catenin; β-catenin; γ-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)—0017-1A/GA733; APC), choriocarcinoma (CEA), epithelial cell cancer (cyclophilin b), gastric cancer (HER2/neu; c-erbB-2; ga733 glycoprotein), hepatocellular cancer (α-fetoprotein), Hodgkins lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (lmp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; prostate-specific membrane antigen (PSMA); HER2/neu; c-erbB-2), pancreatic cancer (p21ras; MUC family; HER2/neu; c-erbB-2; ga733 glycoprotein), renal cancer (HER2/neu; c-erbB-2), squamous cell cancers of cervix and esophagus (viral products such as human papillomavirus proteins), testicular cancer (NY-ESO-1), T-cell leukemia (HTLV-1 epitopes), and melanoma (Melan-A/MART-1; cdc27; MAGE-3; p21ras; gp100$^{Pmel117}$).

In one aspect the invention provides a pharmaceutical composition. The pharmaceutical composition according to this aspect of the invention includes an aerosol formulation of a polymer of repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate.

In certain embodiments the pharmaceutical composition further includes another agent, useful in the treatment of an allergic condition or asthma, commingled with or conjugated to the polymer in the aerosol formulation. Other agents useful in the treatment of an allergic condition or asthma are described above.

An "aerosol formulation" as used herein refers to any suitable preparation that includes droplets or particles of the active ingredient suitable for delivery to a respiratory epithelium. Droplets or particles will generally fall within the range of 2-20 wn in diameter. The aerosol formulation will in general include a therapeutically effective amount of the polymer and a pharmaceutically acceptable carrier, and optionally a propellant, in a container or aerosol delivery system. A therapeutic amount in this circumstance takes into account certain inefficiencies involved in aerosol delivery to a target tissue.

In one aspect the invention provides an aerosol delivery system that includes a container with an interior, an aerosol generator in fluid connection with the interior of the container, and a polymer of repeating units of a charge motif characteristic of *B. fragilis* polysaccharide A (PSA), the motif being a positively charged free amino moiety and a negatively charged moiety selected from the group consisting of carboxyl, phosphate, phosphonate, sulfate and sulfonate, disposed within the interior of the container. The aerosol delivery system can be made to deliver a single dose or a plurality of doses. In one embodiment the inhaler is a metered dose inhaler. In one embodiment the inhaler is a dry powder inhaler. In another embodiment the inhaler is a nebulizer. In yet another embodiment the inhaler is a spray dispenser for topical delivery to a nasal epithelium or other respiratory epithelium. In one embodiment the aerosol delivery system further includes another agent useful in the treatment of an allergic condition or asthma.

In one embodiment the aerosol delivery system includes a vibrational element constructed and arranged to vibrate an aperture plate having a plurality of apertures of defined geometry, wherein one side or surface of the aperture plate is in fluid connection with a solution or suspension of the polymer. See, e.g., U.S. Pat. No. 5,758,637, U.S. Pat. No. 5,938,117, U.S. Pat. No. 6,014,970, U.S. Pat. No. 6,085,740, and U.S. Pat. No. 6,205,999, the entire contents of which are incorporated by reference. Activation of the vibrational element to vibrate the aperture plate causes liquid containing the polymer in solution or suspension to be drawn through the plurality of apertures to create a low-velocity aerosol with a defined range of droplet (i.e., particle) sizes.

Examples of this type of aerosol generator are commercially available from Aerogen, Inc., Sunnyvale, Calif.

In another embodiment the aerosol delivery system includes a pressurized container containing the polymer in solution or suspension. The pressurized container typically has an actuator connected to a metering valve so that activation of the actuator causes a predetermined amount of the polymer in solution or suspension within the container to be dispensed from the container in the form of an aerosol. Pressurized containers of this type are well known in the art as propellant-driven metered dose inhalers (pMDIs or simply MDIs). MDIs typically include an actuator, a metering valve, and a pressurized container that holds a micronized drug suspension or solution, liquefied propellant, and surfactant (e.g., oleic acid, sorbitan trioleate, lecithin). Historically these MDIs typically used chlorofluorocarbons (CFCs) as propellants, including trichlorofluoromethane, dichlorodifluoromethane, and dichlorotetrafluoromethane. Cosolvents such as ethanol may be present when the propellant alone is a relatively poor solvent. Newer propellants may include 1,1,1,2-tetrafluoroethane and 1,1,1,2,3,3,3-heptafluoropropane. Actuation of MDIs typically causes dose amounts of 50 µg-5 mg of active agent in volumes of 20-100 µL to be delivered at high velocity (30 m/sec) over 100-200 msec.

In other embodiments the aerosol delivery system includes an air-jet nebulizer or ultrasonic nebulizer in fluid connection with a reservoir containing the polymer in solution or suspension. Nebulizers (air-jet or ultrasonic) are used primarily for acute care of nonambulatory patients and in infants and children. Air-jet nebulizers for atomization are considered portable because of the availability of small compressed air pumps, but they are relatively large and inconvenient systems. Ultrasonic nebulizers have the advantage of being more portable because they generally do not require a source of compressed air. Nebulizers provide very small droplets and high mass output. Doses administered by nebulization are much larger than doses in MDIs and the liquid reservoir is limited in size, resulting in short, single-duration therapy.

To generate an aerosol from an air-jet nebulizer, compressed air is forced through an orifice over the open end of a capillary tube, creating a region of low pressure. The liquid formulation is drawn through the tube to mix with the air jet and form the droplets. Baffles within the nebulizer remove larger droplets. The droplet size in the airstream is influenced by the compressed air pressure. The various commercially available air-jet nebulizers do not perform equally. This will affect the clinical efficacy of nebulized aerosol, which depends on the droplet size, total output from the nebulizer, and patient determinants.

Ultrasonic nebulizers generate aerosols using high-frequency ultrasonic waves (i.e., 100 kHz and higher) focused in the liquid chamber by a ceramic piezoelectric crystal that mechanically vibrates upon stimulation. Dennis J H et al. (1992) *J Med Eng Tech* 16:63-68; O'Doherty M J et al. (1992) *Am Rev Respir Dis* 146:383-88. In some instances, an impeller blows the particles out of the nebulizer or the aerosol is inhaled directly by the patient. The ultrasonic nebulizer is capable of greater output than the air-jet nebulizer and for this reason is used frequently in aerosol drug therapy. The droplets formed using ultrasonic nebulizers, which depend upon the frequency, are coarser (i.e., higher MMAD) than those delivered by air-jet nebulizers. The energy introduced into the liquid can result in an increase in temperature, which results in vaporization and variations in concentrations over time. This concentration variation over time is also encountered in jet nebulizers but is due to water loss through evaporation.

The choice between solution or suspension formulations in nebulizers is similar to that for the MDI. The formulation chosen will affect total mass output and particle size. Nebulizer formulations typically contain water with cosolvents (ethanol, glycerin, propylene glycol) and surfactants added to improve solubility and stability. Commonly an osmotic agent is also added to prevent bronchoconstriction from hypoosmotic or hyperosmotic solutions. Witeck T J et al. (1984) *Chest* 86:592-94; Desager K N et al. (1990) *Agents Actions* 31:225-28.

In yet other embodiments the aerosol delivery system includes a dry powder inhaler in fluid connection with a reservoir containing the polymer in powder form. The dry powder inhaler device may eventually replace MDIs for some indications in response to the international control of chlorofluorocarbons in these latter products. Notably, this device can only deliver a fraction of its load in a respirable size range. Powder inhalers will usually disperse only about 10 to 20% of the contained drug into respirable particles. The typical dry powder inhaler device consists of two elements: the inhalation appliance to disperse unit doses of the powder formulation into the inspired airstream, and a reservoir of the powder formulation to dispense these doses. The reservoir typically can be of two different types. A bulk reservoir allows a precise quantity of powder to be dispensed upon individual dose delivery up to approximately 200 doses. A unit dose reservoir provides individual doses (e.g., provided in blister packaging or in gelatin capsule form) for inhalation as required. The hand-held device is designed to be manipulated to break open the capsule/blister package or to load bulk powder followed by dispersion from the patient's inspiration. Airflow will deaggregate and aerosolize the powder. In most cases, the patient's inspiratory airflow activates the device, provides the energy to disperse and deagglomerate the dry powder, and determines the amount of medicament that will reach the lungs.

Dry powder generators are subject to variability because of the physical and chemical properties of the powder. These inhalers are designed to meter doses ranging from 200 µg to 20 mg. The preparation of drug powder in these devices is very important. The powder in these inhalers requires efficient size reduction that is also needed for suspensions in MDIs. Micronized particles flow and are dispersed more unevenly than coarse particles. Therefore the micronized drug powder can be mixed with an inert carrier. This carrier is usually α-lactose monohydrate, because lactose comes in a variety of particle size ranges and is well characterized. Byron P R et al. (1990) *Pharm Res* 7(suppl):S81. The carrier particles have a larger particle size than the therapeutic agent to prevent the excipient from entering the airways. Segregation of the two particles will occur when turbulent airflow is created upon patient inhalation through the mouthpiece. This turbulence of inspiration will provide a certain amount of energy to overcome the interparticulate cohesive and particle surface adhesive forces for the micronized particles to become airborne. High concentrations of drug particles in air are easily attained using dry powder generation, but stability of the output and the presence of agglomerated and charged particles are common problems. With very small particles, dispersion is difficult because of electrostatic, van der Waals, capillary, and mechanical forces that increase their energy of association.

An example of a dry powder inhaler aerosol generator suitable for use with the present invention is the Spinhaler powder inhaler available from Fisons Corp., Bedford, Mass.

Polymers Useful in the Invention

The zwitterionic polymers useful in the invention have been described, in part, in U.S. Pat. Nos. 5,679,654 and 5,700,787, both issued to Tzianabos et al., and published international patent applications WO 00/59515 and WO 03/075953, the entire contents of all of which are incorporated herein by reference. Briefly, they encompass both polysaccharides, peptides, and a synthetic peptidoglycan characterized by their inclusion of a specific charge motif. The necessary motif was originally identified to include a positively charged free amino group and a negatively charged group on a polysaccharide repeating unit, such as is characteristic of capsular polysaccharide A (PSA) of *B. fragilis*. This same charge motif was subsequently demonstrated to be operative in the context of a peptide polymer.

A "polymer" as used herein is a compound having a linear backbone of individual units which are linked together by linkages. The term "backbone" is given its usual meaning in the field of polymer chemistry. The polymers can be homogeneous or heterogeneous in backbone composition, so long as they have the requisite charge motif. In some embodiments the polymers can differ from those polymers conventionally known in the art because the polymers of the invention can have non-polymeric compounds incorporated into the backbone. For instance, the polymer of the invention can be composed entirely of amino acids except for a region which contains an organic linker that links two sets of amino acids together. In one embodiment the polymers are homogeneous in backbone composition, including, for example, peptides, polysaccharides, and nucleic acids. A "peptide" as used herein is a polymer of linked amino acids. An "oligopeptide" as used herein is a peptide polymer of 2 to about 50 amino acids. A peptide thus refers generally to both polypeptides and to oligopeptides. A "polysaccharide" as used herein is a polymer of linked sugars (saccharides). A "nucleic acid" as used herein is a polymer of linked nucleotides, such as deoxyribonucleotides or ribonucleotides.

The polymers can be composed of repeating units of the charge motif. For example, the entire polymer can be composed of the repeating charge motif. A "unit" is used herein consistently with its known meaning in the art to indicate a building block of a polymer. Each unit can include one or a plurality (i.e., a set) of subunits, wherein a subunit is an individual moiety, e.g., a saccharide, an amino acid, a nucleotide, etc. A polymer composed of repeating units is one which is composed entirely of units which occur at least twice within the polymer. The repeating units of the polymer can be identical or non-identical repeating units. An "identical repeating unit" as used herein is a set of subunits that is repeated within the polymer and in which all of the subunits have the identical composition and are positioned in the identical order to the subunits of the other sets of subunits. A "non-identical repeating unit" as used herein is a set of subunits that is repeated within the polymer and in which all of the subunits do not have the identical composition and/or are not positioned in the identical order to the subunits of the other sets of subunits. Some of the subunits of a non-identical repeating unit can have the identical order and/or position as the subunits of the other sets, as long as not all the subunits are identical. When used in the context of this invention, a polymer having non-identical repeating units is a polymer which can have all non-identical repeating units or a combination of identical and non-identical repeating units.

The polymer includes at least two repeating charge motifs. A "repeating charge motif" as used herein is a motif composed of a positively charged free amino moiety and a negatively charged moiety. The motif can be composed of a dually charged single subunit or of multiple subunits, one subunit having the positively charged free amino group and a second subunit having the negative charge. In the case that the charges are present on different subunits, the subunits can be adjacent to one another or they can be separated by intervening subunits. In one embodiment the intervening subunits are neutral subunits. A neutral subunit is a subunit which does not carry a positive charge or a negative charge. The charged subunits of the motif can be separated by any number but preferably by less than 10 neutral subunits. A repeating charge motif can be present in any orientation within the polymer. For instance, in a polymer having two repeating charge motifs separated by neutral subunits the polymer can have the following sequence: a positive charge first followed by a negative charge, followed by neutral subunits followed by a negative charge and finally a positive charge. Alternatively the polymer can have the following sequence: a positive charge first followed by a negative charge, followed by neutral subunits, followed by a positive charge and finally a negative charge, etc.

A "positively charged free amino moiety" as used herein refers to a primary amine. A "negatively charged moiety" as used herein refers to any negatively charged group, including but not limited to carboxyl, phosphate, phosphonate, sulfate, and sulfonate. In one embodiment the negatively charged moiety is a carboxyl group. Positively charged amino acids having a free amino group include but are not limited to lysine (K), arginine (R), asparagine (N), and histidine (H). Negatively charged amino acids include but are not limited to aspartic acid (D) and glutamic acid (E).

The polymer has at least two repeating charge motifs but generally can have any number greater than two. The whole polymer, for instance, can be composed of repeating charge motifs. Alternatively the polymer can be composed of any number of repeating charge motifs between two and the number for which the entire polymer is composed of repeating charge motifs (which of course will depend on the size of the polymer). The polymer can have, for instance, at least 10, 15, 20, 25, 30, 35, etc., repeating charge motifs.

The region between the repeating charge motifs can be composed of repeating charge motifs, other units, or a mixture thereof. The region can be, for instance, an intervening sequence that is neutral. The intervening sequence can be the same type of unit as the other units of the polymer, or it can be completely different. For instance, it can be a non-polymeric organic moiety.

In one embodiment the polymer can be a polysaccharide formed of repeating units of a maximum of ten saccharides, wherein each repeating unit includes at least one free amino moiety and one negatively charged moiety selected from the group consisting of carboxyl, phosphate and phosphonate. The polymer is optionally free from complexation as part of a *B. fragilis* capsular polysaccharide complex. In certain embodiments the polysaccharide is formed of repeating units of a maximum of five monosaccharides. Such polysaccharides occur in nature and can be isolated. One such polysaccharide is a capsular polysaccharide A (PSA) of the *B. fragilis* capsular polysaccharide complex. In nature PSA occurs only in complexed form, tightly bound to the *B. fragilis* capsular polysaccharide B (PSB). Unlike isolated PSA or isolated PSB, the A:B capsular polysaccharide complex was previously found not to induce cross-protection to infection with other bacteria. Thus, in one embodiment the invention contemplates administration of isolated PSA, free from complexation as part of a *B. fragilis* capsular polysaccharide complex.

The polysaccharides useful according to the invention also can be synthesized from naturally occurring polysaccharides that do not possess the requisite motif. For example, certain naturally occurring polysaccharides have a negatively charged group and at least one N-acetyl moiety on each repeating unit. Such polysaccharides can be de-N-acetylated to convert the N-acetyl moiety to a free amino moiety, thereby creating the necessary structural motif for use according to the invention. Other naturally occurring polysaccharides include imine groups which can be reduced to form a free amino moiety, thereby creating together with a negatively charged group the structural motif necessary for usefulness according to the invention.

Thus, the invention contemplates methods for preparing pharmaceuticals by selecting polysaccharides having repeating units of a maximum of ten saccharides, each unit having at least one negatively charged moiety selected from the group consisting of carboxyl, phosphate and phosphonate. Each repeating unit also includes a moiety that can be modified to form a free amino moiety. Such modified polysaccharides then are mixed with pharmaceutically acceptable carriers, preferably in amounts to form effective doses for protecting a subject against allergic condition or asthma.

Polysaccharides useful according to the present invention include those naturally occurring polysaccharides that include the requisite charged groups. These polysaccharides can be derived from bacterial sources. Bacteria used as starting materials to obtain capsular polysaccharides can be obtained commercially from a number of sources. For example, the *B. fragilis*, NCTC 9343 and ATCC 23745 can be obtained from the National Collection of Type Cultures (London, England) and the American Type Culture Collection (ATCC, Manassas, Va.). Polysaccharide A and polysaccharide B can be purified from the above bacteria based on the protocol of Pantosti A et al. (1991) *Infect Immun* 59:2075-82, modified slightly as described in the Examples section below.

In addition to the naturally occurring polysaccharides, polysaccharide repeating units that consist of at least one N-acetyl sugar and at least one uronic acid (sugar with a negatively charged carboxyl group) can be modified to produce the immune response of the present invention. A polysaccharide repeating unit containing at least one N-acetyl sugar and at least one uronic acid can be de-N-acetylated to create a free amino group and thus will yield a polysaccharide with the correct charge motif. Molecules which can be de-N-acetylated include *Salmonella typhi* capsular polysaccharide (Vi antigen), *Escherichia coli* K5 capsular polysaccharide, *Staphylococcus aureus* type 5 capsular polysaccharide, Group B *Streptococcus* type III capsular polysaccharide, and *Rhizobium meliloti* exopolysaccharide II.

Bacterial polysaccharides which possess imine groups in addition to free carboxyl groups can be modified and used to produce the immune response of the present invention. Many of the *Pseudomonas aeruginosa* O-specific side chains possess imine groups. For those polysaccharides that contain imine moieties, free amino groups can be formed by conventional chemistry techniques known to those of ordinary skill in the art. One suitable method involves the use of sodium borohydride ($NaBH_4$). The imine group can be reduced with sodium borohydride to create a free amino group ($NH3^+$). This is done by adding in excess of 5 mg of borohydride to polysaccharide dissolved in distilled water while stirring at room temperature for 2 hours. The mixture is then dialyzed against water and freeze dried. An example of a compound which may be reduced with sodium borohydride to create free amino groups is *Pseudomonas aeruginosa* Fisher 7.

The polysaccharides useful in the invention can be delivered in mixtures of more than one polysaccharide. A mixture can consist of several polysaccharides.

As discussed above, naturally occurring polysaccharides can be modified to yield immunomodulators useful in the invention. *Salmonella typhi* has a capsular polysaccharide (Vi antigen) that is formed entirely of repeating monomers of galactosaminuronic acid. This acid includes a carboxylic moiety and an N-acetyl moiety. The N-acetyl moiety can be modified to yield a free amino group such that each monomeric repeating unit then has both a positively and negatively charged group.

Polysaccharides that are complexes exist and can be modified to yield immunomodulators useful in the invention. *Esherichia coli* K5 capsular polysaccharide is formed of repeat units of a complex of glucuronic acid and glucosamine linked together in 1-4 linkages. The glucuronic acid carries a carboxylic acid moiety and the glucosamine carries an N-acetyl group, which can be modified to form a free amino group. When so modified, a complex repeat unit having both a negatively charged moiety (on the first sugar) and a free amino group (on the second sugar) is formed.

Polysaccharides that are trimers exist and can be modified to yield immunomodulators useful in the invention. *Staphylococcus aureus* type 5 capsular polysaccharide is formed of repeat units of a trimer of mannosaminuronic acid—fucosamine—fucosamine. The mannosaminuronic acid carries a carboxylic acid moiety and the fucosamines carry N-acetyl moieties which can be modified to form free amino moieties. When so modified, a trimeric repeat unit having a negatively charged moiety (on the first sugar) and at least one positively charged moiety (on the second and third sugars) is formed. In a similar manner, *Pseudomonas aeruginosa* O-antigens can be modified to yield immunomodulators useful in the invention. Examples include trimers that carry carboxylic acid moieties and imine moieties which can be modified to yield free amino groups. Fisher immunotype 7, Lanyi-Bergan O2a, O2b and Lanyi-Bergan O2d, and 2f have polysaccharides formed of trimeric repeat units with carboxylic acid moieties on the first and second sugars and an imine moiety on the first sugar. (The third sugar is free of a charged moiety; all sugars also carry an N-acetyl moiety). For example, the first sugar can be modified so as to carry both a free amino moiety and the carboxylic acid moiety. Likewise the N-acetyl groups could be modified to yield a different arrangement useful according to the invention.

Polysaccharides that have longer repeat units such as tetramers and pentamers also can be modified as described above. It is believed that repeat units up to decimers are useful according to the invention. In addition, repeat units including side chain sugars also are useful, including those wherein-one or both of the free amino and negatively charged moieties are located on such side chains. Furthermore, such side chains carrying the charged moieties need not be sugars, although in one embodiment at least the backbone of the repeat unit is made up of only sugars.

In certain embodiments the repeat unit has no more than three free amino groups, and, in one embodiment, no more than two such groups. In one embodiment there is at least one negatively charged group for each free amino group.

The starting materials further need not be derived from bacterial origin. Any polysaccharides carrying carboxylic acid moieties and N-acetyl or imine groups can be modified as described above.

Specific examples together with chemical names and structural formulas are provided in U.S. Pat. Nos. 5,679,654 and 5,700,787, both issued to Tzianabos et al.

De-N-acetylation can be accomplished by conventional chemistry techniques well known to those of ordinary skill in the art. One suitable method involves the use of alkali with or without sodium borohydride. Twenty mg of polysaccharide is dissolved in 2M NaOH (3 ml) and sodium borohydride is added (50 mg). The solution is heated to 100° C. for five hours. Following neutralization with acid, the solution is dialyzed against distilled water in the cold and freeze-dried. DiFabio J L et al. (1989) *Can J Chem* 67:877-82.

Naturally occurring polysaccharides also can be used without modification in the methods of the invention and in forming the pharmaceutical preparations of the invention. Non-limiting examples include *Shigella sonnei* Phase I lipopolysaccharide O-antigen; *Streptococcus pneumoniae* type I capsular polysaccharide (CP1); and *Streptococcus pneumoniae* group antigen:C substance, as described in U.S. Pat. Nos. 5,679,654 and 5,700,787, both issued to Tzianabos et al.

A polysaccharide that does not have solely a sugar backbone but still is believed to be useful according to the invention is *Trypanosoma cruzi* lipopeptidophosphoglycan.

The naturally occurring polysaccharides that can be used without modification also can be modified to selectively add, subtract or modify various moieties, including free amino moieties, negatively charged moieties or other moieties. Examples include adding free amino moieties by modifying existing N-acetyl groups or imine groups or forming hydroxymethyl groups from alcohol groups.

Polysaccharides useful according to the invention can be obtained from commercial sources or can be isolated and derived from natural sources such as bacteria, fungi, seaweed and the like. The following is a list of bacterial polysaccharides and references which detail the isolation and preparation of such polysaccharides.

*Bacteroides fragilis* PSA1, also previously referred to simply as PSA, has a tetrasaccharide repeating unit containing one cationic free amine and one anionic carboxylate in each repeating unit. Tzianabos A O et al. (1992) *J Biol Chem* 267:18230-5.; U.S. Pat. Nos. 5,679,654 and 5,700,787.

*Bacteroides fragilis* PSA2 has a pentasaccharide repeating unit containing mannoheptose, N-acetylmannosamine, 3-acetamido-3,6-dideoxyglucose, 2-amino-4-acetamido-2,4,6-trideoxygalactose, fucose, and 3-hydroxybutanoic acid. Wang Y et al. (2000) *Proc Natl Acad Sci USA* 97:13478-83; Kalka-Moll W M et al. (2001) *Infect Immun* 69:2339-44. PSA2 is zwitterionic and carries one cationic free amine and one anionic carboxylate in each repeating unit.

*Bacteroides fragilis* PSB has as hexasaccharide repeating unit and carries one cationic free amine and two negative charges in each repeating unit. Tzianabos A O et al. (1992) *J Biol Chem* 267:18230-5; U.S. Pat. Nos. 5,679,654 and 5,700,787.

*Salmonella typhi* capsule (Vi antigen), Szu S C et al. (1991) *Infect Immun* 59:4555-61.

*Escherichia coli* K5 capsule, Vann W et al. (1981) *Eur J Biochem* 116:359-64.

*Staphylococcus aureus* type 5 capsule, Fournier J-M et al. (1987) *Ann Inst Pasteur Microbiol* 138:561-7.

*Rhizobium meliloti* expolysaccharide II, Glazebrook J et al. (1989) *Cell* 65:661-72.

Group B *streptococcus* type III, Wessels M R et al. (1987) *J Biol Chem* 262:8262-7.

*Pseudomonas aeruginosa* Fisher 7 O-specific side-chain, Knirel Y A et al. (1987) *Eur J Biochem* 167:549-61.

*Shigella sonnei* O-specific side chain, Kenne L et al. (1980) *Carbohydr Res* 78:119-26.

*Streptococcus pneumoniae* type I capsule, Lindberg B et al. (1980) *Carbohydr Res* 78:111.

*Streptococcus pneumoniae* group antigen, Jennings H J et al. (1980) *Biochemistry* 19:4712-9.

In another embodiment the polymer can be a peptide having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues. In one embodiment the repeating charge motif is present as a repeating set of amino acids. In one particular embodiment the repeating charge motif is present as a repeating set of lysine (K)-aspartic acid (D) repeats, i.e., $(K-D)_n$. In one embodiment the repeating charge motif is present as a repeating set of lysine (K)-$(Xaa)_m$-aspartic acid (D) repeats, i.e., $[K—(Xaa)_m-D]_n$, where K, Xaa, D, m, and n are as defined above.

Also useful in the practice of the invention is the synthetic peptidoglycan polymer Compound 15 described in published international patent application WO 03/075953. A method for preparation and verification of Compound 15 is provided in Example 1 of that publication.

Any zwitterionic polymer useful according to the methods, uses, and compositions of the invention can optionally be present as a hydrate of the polymer, as a pharmaceutically acceptable salt of the polymer, or as any combination thereof.

Administration

When administered, the formulations of the invention are applied in pharmaceutically acceptable solutions. Such preparations can routinely contain pharmaceutically acceptable concentrations of salt, buffering agents, preservatives, compatible carriers, adjuvants, and optionally other therapeutic ingredients.

The polymer can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V); and thimerosal (0.004-0.02% W/V).

The polymer preparation of the present invention can be a pharmaceutical composition having an effective amount of a polymer optionally included in a pharmaceutically acceptable carrier. The term "pharmaceutically-acceptable carrier" as used herein means one or more compatible solid or liquid filler, dilutants or encapsulating substances which are suitable for administration to a human or other animal.

In the present invention, the term "carrier" denotes an organic or inorganic ingredient, natural or synthetic, with which the active ingredient is combined to facilitate the application. The components of the pharmaceutical compositions also are capable of being commingled with the polymers of the present invention, and with each other, in a manner such that there is no interaction which would substantially impair the desired pharmaceutical efficiency.

Compositions suitable for parenteral administration conveniently include a sterile aqueous preparation of the polymer, which can be isotonic with the blood of the recipient. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables. Carrier formulations suitable for subcutaneous, intramuscular, intraperitoneal, intravenous, etc. administrations can be found in *Remington's Pharmaceutical Sciences*, Mack Publishing Company, Easton, Pa.

Other immunomodulators such as cytokines can be delivered in conjunction with the polymers of the invention, and "cocktails" including the polymers and the cytokines are contemplated. The cytokines contemplated are those that will enhance the beneficial effects that result from administering the polymers according to the invention. Cytokines are factors that support the growth and maturation of cells, including lymphocytes. Important to the invention herein is modulating T cell development, as the methods of the invention appear to be T-cell-mediated. The cytokines can act directly on T cells or indirectly on T cells through other cells. It is believed that the addition of cytokines will augment cytokine activity stimulated in vivo by carrying out the methods of the invention. In one embodiment the cytokine is interleukin-10.

Other agents useful in the treatment of an allergic condition and asthma can be delivered in conjunction with the polymers of the invention, and "cocktails" including the polymers and the other agents are contemplated. The other agents contemplated are those that will enhance the beneficial effects that result from administering the polymers according to the invention. More particularly, the other agents can be selected from glucocorticoids, beta adrenergic agonists, methylxanthines, anticholinergics, cromolyn, nedocromil, antihistamines, IL-10, and anti-IgE. Specific examples of such agents are disclosed above. Many of these other agents are already available as aerosol formulations.

The preparations of the invention are administered in effective amounts. It is believed that doses of polymer ranging from 1 nanogram/kilogram to 100 milligrams/kilogram, depending upon the mode of administration and molecular weight of the polymer, will be effective. The absolute amount will depend upon a variety of factors including the number of doses and individual patient parameters including age, physical condition, size and weight. These are factors well known to those of ordinary skill in the art and can be addressed with no more than routine experimentation.

For example, administration of CP1 in mice for the treatment of asthma has been found to be effective at doses of about 1-10 mg/kg/day when administered subcutaneously, and at doses of about 10-50 mg/kg/d when administered by aerosol to the lungs.

Multiple doses of the pharmaceutical compositions of the invention are contemplated. The invention has been shown to be effective, for example, with multiple doses of polymer administered over a three-week period. It has been discovered, for example, that in mice the suppressive activity achieved with three daily doses generally wanes within 14 days of the last dose. Thus for chronic conditions such as allergy and asthma the invention specifically includes methods of chronic administration of the polymer, alone or with an adjunctive therapy, over a period of days, weeks, months, or even years. In one embodiment the polymer is administered to a subject on a daily basis. In various embodiments the polymer is administered to a subject on an every other day, an every third day, every fourth day, every fifth day, every sixth day, twice-a-week, or three-times-a-week basis. In one embodiment the polymer is administered to a subject on a weekly basis. In one embodiment the polymer is administered to a subject on a bi-weekly basis. Other schedules not listed here are also contemplated by the invention, provided they include at least two doses administered within two weeks of each other. Such other schedules need not be regular but may instead be guided, for example, by symptoms of the condition that is to be treated.

A variety of administration routes are generally available. The particular mode selected will depend, of course, upon the particular polysaccharide selected, the particular condition being treated, and the dosage required for therapeutic efficacy. The methods of this invention, generally speaking, can be practiced using any mode of administration that is medically acceptable, meaning any mode that produces effective modulation of an immune response without causing clinically unacceptable adverse effects. Modes of administration include enteral and parenteral routes. The term "enteral" specifically includes, but is not limited to, oral. The term "parenteral" includes, without limitation, subcutaneous, intradermal, intravenous, intramuscular, and intraperitoneal injection or infusion techniques. Mucosal, topical, intralesional, and transdermal administration are also included as parenteral routes of administration.

As discussed above, aerosol delivery is specifically contemplated by the invention, particularly but not exclusively for the method of treating asthma. Aerosol delivery specifically includes both pulmonary airway delivery by inhalation and intranasal delivery, e.g., by inhalation or insufflation.

The compositions can conveniently be presented in unit dosage form and can be prepared by any of the methods well known in the art of pharmacy. All methods include the step of bringing the active polymer into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer can be stored lyophilized and reconstituted for use.

Other delivery systems can include time-release, delayed release or sustained release delivery systems. Such systems can avoid repeated administrations of the polymers of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants, and the like. Specific examples include, but are not limited to: (a) erosional systems in which the polymer is contained in a form within a matrix, found in U.S. Pat. No. 4,452,775 (Kent); U.S. Pat. No. 4,667,014 (Nestor et al.); and U.S. Pat. No. 4,748,034 and U.S. Pat. No. 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

EXAMPLES

Sources of Bacteria, Isolation and Modification of Polysaccharides

B. fragilis NCTC 9343 and ATCC 23745 were originally obtained from the National Collection of Type Cultures (London, England) or the American Type Culture Collection (ATCC, Manassas, Va.). Microorganisms were stored at −80° C. in peptone-yeast or brain heart infusion broth until used, and grown anaerobically as previously described. Pantosti et al. *Infect Immun* 59:2075 (1991). The CPC from *B. fragilis* NCTC 9343 or ATCC 23745 was isolated by hot phenol/water extraction and subsequent purification of PSA performed as previously described. Tzianabos, A et al. *J Biol Chem* 267: 18230 (1992).

The *S. pneumoniae* type 1 capsular polysaccharide (CP1) and other pneumococcal polysaccharides were obtained from ATCC.

Chemical modifications of polysaccharides to produce molecules with altered charges have been described previously. Taylor R et al. (1972) *Biochemistry* 11:1383 (carbodiimide reduction); Baumann H et al. (1992) *Biochemistry* 31:4081 (N-acetylation and deamination).

Postoperative Surgical Adhesion Suppression by *Streptococcus pneumoniae* Type 1 CP (CP1)

Rats (10 per group) were treated with saline (100 µl), pectin (polygalacturonic acid, 100 µg in 100 µl saline), or the *Streptococcus pneumoniae* type 1 CP (a trisaccharide repeating unit with two galacturonic acid residues and a 2-acetamido-4-amino-2,4,6-trideoxygalactose, 80 kDa, 100 µg in 100 µl saline) subcutaneously at −24 h, 0 h, and +24 h relative to surgical manipulation. Adhesions were induced as previously described with some modification. Kennedy R et al. (1996) *Surgery* 120:866-70. Briefly, a 3 cm midline incision was made into the abdominal cavity and the cecum exposed. The cecum was abraded with surgical gauze until punctate hemorrhages were visible. The cecum was inserted into the peritoneal cavity and the apposing abdominal wall abraded in a similar manner. Following this procedure, sterilized rat cecal contents (0.5 ml) was added to the peritoneal cavity as previously described. Onderdonk A B et al. (1982) *J Clin Invest* 69:9-16. The wound was closed with 4.0 silk sutures. Animals were sacrificed six days later and examined for the formation of adhesions. Adhesions were scored as previously described on a scale of 0 to 5 as follows: 0, no adhesions; 1, thin filmy adhesion; 2, more than one thin adhesion; 3, thick adhesion with focal point; 4, thick adhesion with planar attachment; and 5, very thick vascularized adhesions or more than one planar adhesion. Kennedy R et al. (1996) *Surgery* 120:866-70.

T Cell Transfer Studies

Splenic T cells isolated from saline or polysaccharide treated animals were fractionated, counted, and transferred via the intracardiac route.

Example 1

Reduction of Post-Surgical Adhesion Formation by Zwitterionic Polysaccharide is Dependent on T Cells and IL-10

Male Lewis rats were injected subcutaneously with saline or CP1 (50 µg/rat) −24, 0, and +24 hours relative to cecal abrasion surgery. Animals were examined for adhesion formation six days later and scored for the severity of adhesions as described. Results are shown in FIG. 1A. Left panel: saline-treated animals exhibited numerous, dense vascularized adhesions involving the cecum and apposing abdominal wall. Right panel: CP1-treated rats exhibited fewer and less severe adhesions.

Figure 1B:
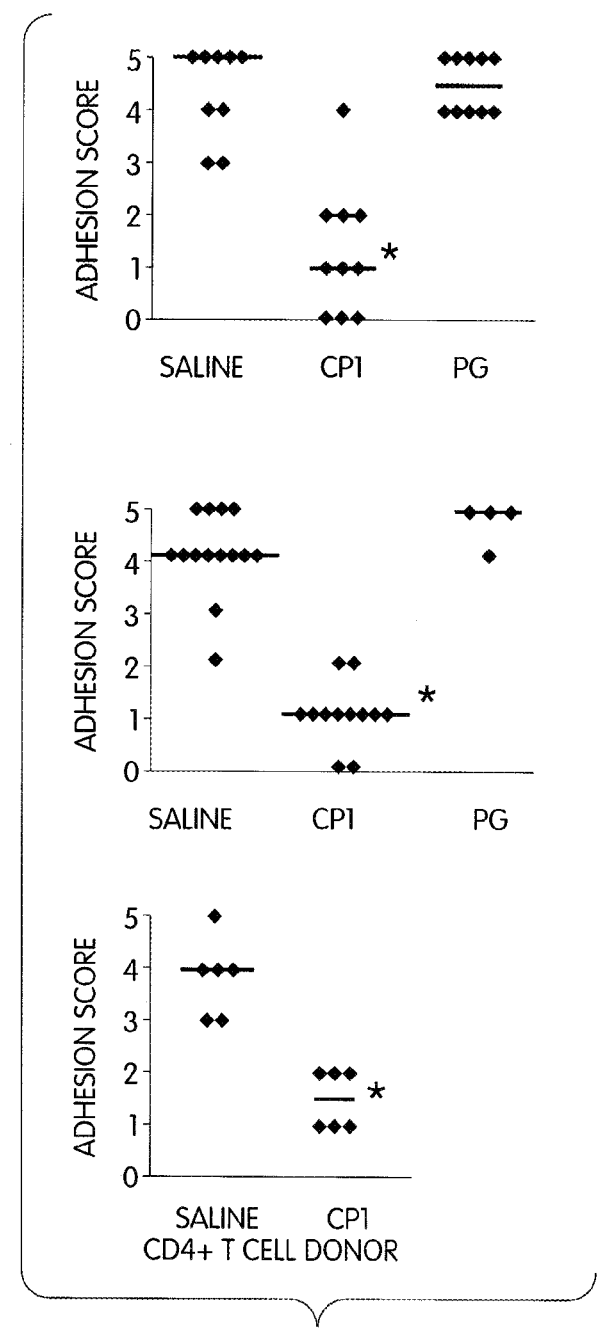
FIG. 1B is three graphs depicting adhesion scores in animals treated with saline, CP1, or non-zwitterionic control polysaccharide PG (left panel, rats; middle panel, mice) and in mice treated with CD4+ T cells transferred from mice treated with saline or CP1 (right panel). *$P<0.001$

FIG. 1B shows that CP1 prevents adhesion formation in a CD4+ T cell-dependent manner. Left panel: adhesions scores of Lewis rats treated with CP1 or a control non-zwitterionic polysaccharide, PG. Each point represents a single animal and the bar represents the median score. CP1-treated animals had significantly lower adhesion scores than saline or PG-treated animals ($P<0.001$). Middle panel: C57BL/6 mice were treated with saline, CP1, or PG in a similar manner and subjected to cecal abrasion surgery. Mice treated with CP1 had significantly lower adhesion scores compared with saline or PG-treated animals (*$P<0.001$). Right panel: Transfer of CD4+ T cells from mice treated with CP1 conferred protection compared with those animals that received CD4+ T cells from saline-treated animals (*$P=0.001$).

Figure 1C:
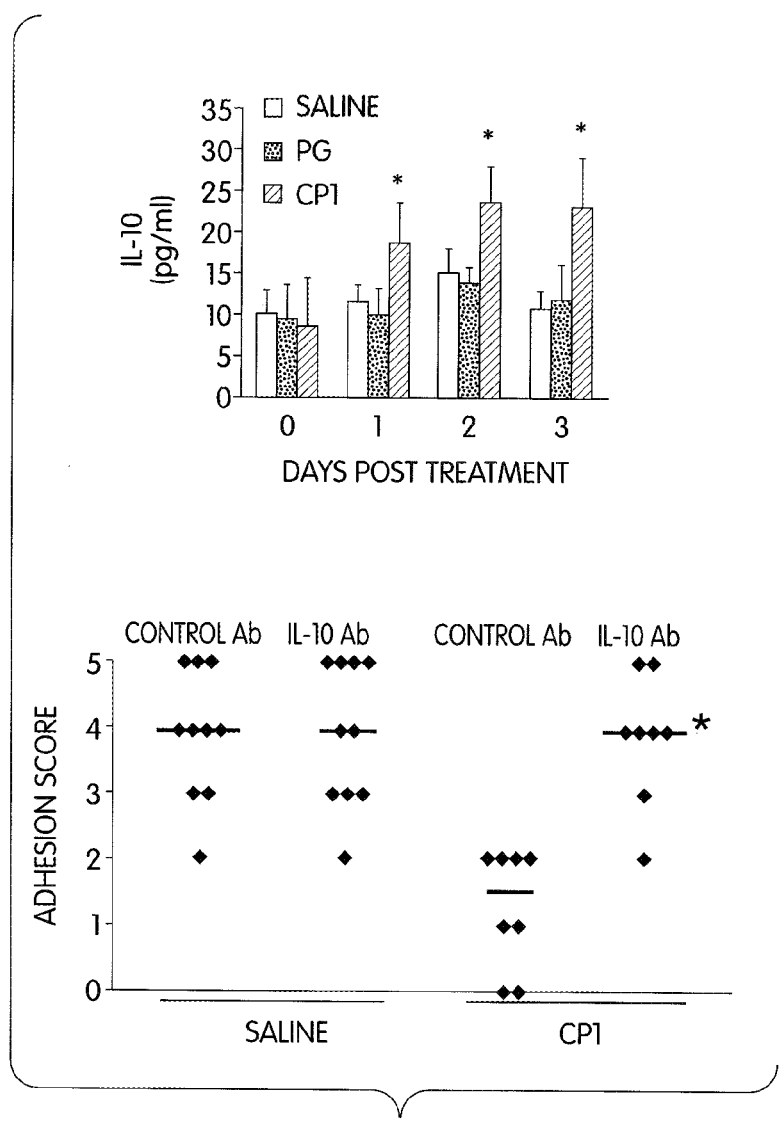
FIG. 1C is a pair of graphs depicting the role of IL-10 in the prevention of adhesions. Left panel, *P<0.02; right panel, *P<0.001.

FIG. 1C shows the role of IL-10 in the prevention of adhesions. Left panel: CP1 induces IL-10 in the peritoneal cavities of mice compared with saline or PG treatment. Animals (n=5/group) were treated for 3 successive days with 50 µg of CP1 or PG and peritoneal fluid harvested for 3 days following the final dose. IL-10 levels were assessed by ELISA. CP1 elicited higher levels of IL-10 than saline or PG treatment (*$P<0.02$). Right panel: Protection by CP1 is abrogated by anti-IL-10 treatment. Mice were treated with saline or CP1 as described above and treated via the intraperitoneal route with a monoclonal antibody (mAb) specific for IL-10 (200 µg at t=0, 24, 48, and 72 hours with respect to cecal abrasion surgery). Treatment with the IL-10-specific monoclonal antibody resulted in significantly higher adhesion scores compared to CP1-treated animals that received the isotype control antibody (*$P<0.001$).

Figure 1D:
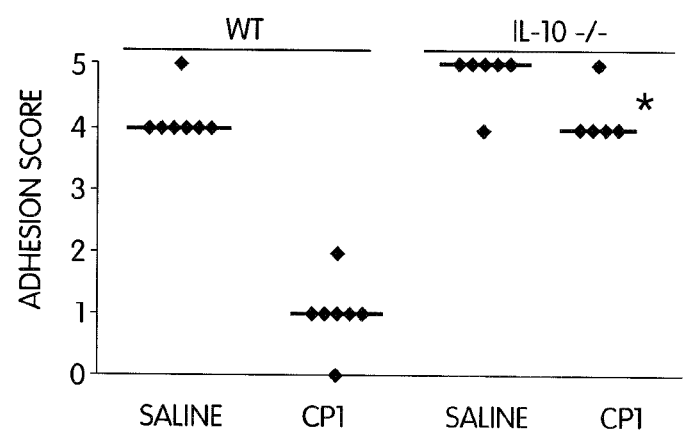
FIG. 1D is a graph depicting adhesion scores in wildtype (WT) and IL-10$^{-/-}$ mice treated with saline or CP1. *P=0.03

FIG. 1D shows that $IL10^{-/-}$ mice treated with CP1 were not protected against adhesion formation compared to littermate wildtype (WT) control mice (*$P=0.003$).

Example 2

Role of Treg Cells in the Prevention of Surgical Adhesions

Figure 2A:
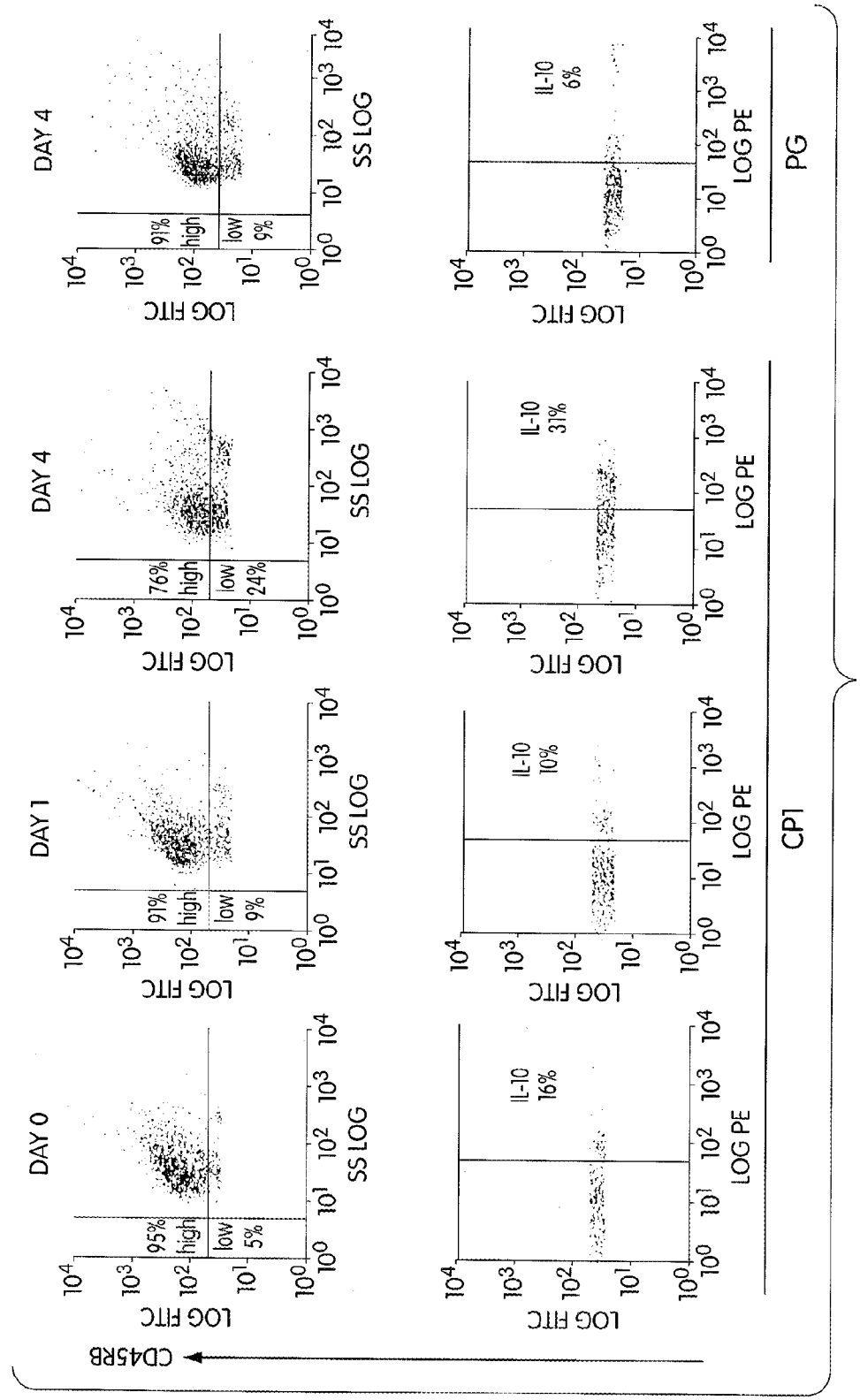
FIG. 2A is a series of graphs depicting results of flow cytometry analyses of CD4+ T cells isolated from mice treated with CP1 or PG and stained for surface CD45RB (upper panels) and intracellular IL-10 (lower panels).

Mice were treated with CP1 or PG (50 µg/dose via the subcutaneous route) and splenic CD4+ T cells isolated and analyzed by flow cytometry for CD45RB surface expression and intracellular IL-10 levels. Results are shown in FIG. 2A. Upper panels: Treatment with CP1 increases the proportion of Treg cells, while decreasing the proportion of $CD45RB^{hi}$ T cells. Treatment with PG did not affect this proportion (day 4 following treatment is shown). Lower panels: Treatment with CP1 increases production of IL-10 from $CD45RB^{lo}$ cells, while PG does not. IL-10 production peaked at day 4 following treatment.

Figure 2B:
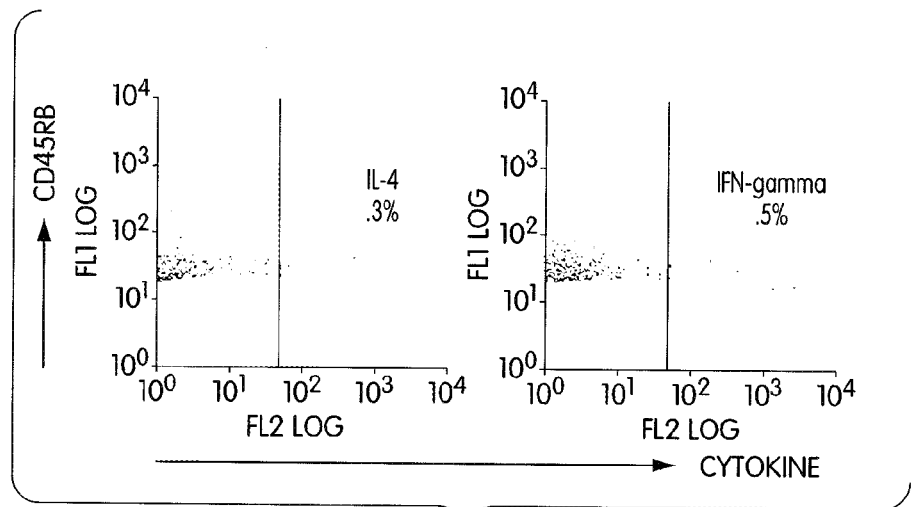
FIG. 2B is a pair of graphs depicting results of flow cytometry analysis of IL-4 (left) and IFN-γ (right) in CD4+ CD45RB$^{lo}$ T cells as measured 4 days after in vivo administration of CP1.

FIG. 2B shows that treatment with CP1 does not elicit IL-4 or IFN-γ from Treg cells. CD4+CD45RB$^{lo}$ T cells were analyzed daily following treatment. Results from Day 4 are shown.

Figure 2C:
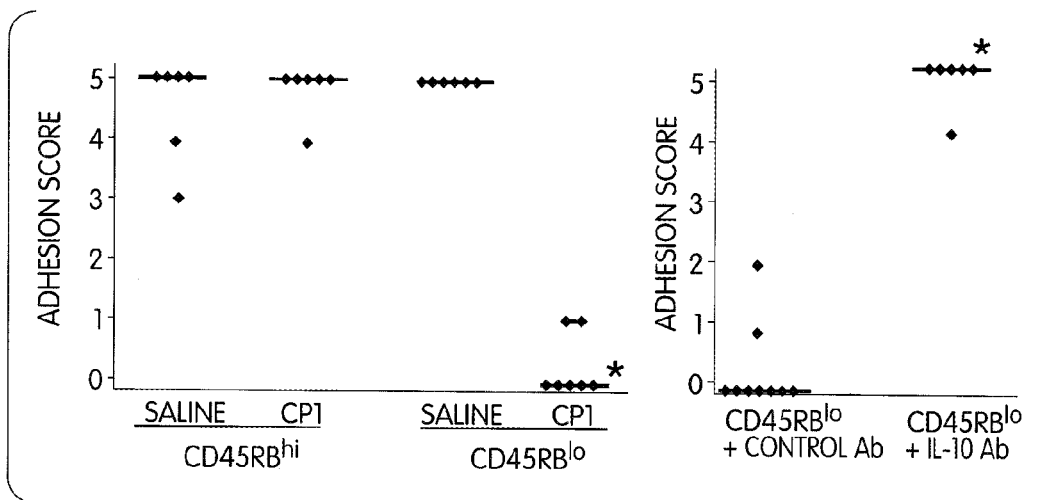
FIG. 2C is a pair of graphs depicting adhesion scores in mice treated with CD45RB$^{hi}$ or CD45RB$^{lo}$ cells transferred from mice treated with saline or CP1 (left panel) and abrogation of protective effect of transferred CD45RB$^{lo}$ cells in the presence of anti-IL-10 antibody (right panel). Left panel, *P<0.001; right panel, *P=0.0002.

FIG. 2C shows that Treg cells transfer protection against adhesion formation in an IL-10 dependent manner. Left panel: Groups of mice were treated as above with saline or CP1 and splenic CD4+ T cells isolated one day following the final treatment. Cells were stained with CD45RB-specific antibody and high (hi) and low (lo) expressing populations isolated by FACS. Each population was then transferred via the intracardiac route and animals subjected to cecal abrasion surgery 24 hours later. Animals receiving CD45RB$^{hi}$ T cells from saline- or CP1-treated animals developed adhesions. Adhesions also developed in mice that received CD45RB$^{lo}$ T cells from saline-treated mice. Mice receiving CD45RB$^{lo}$ T cells from animals treated with CP1 had significantly lower adhesion scores compared with mice receiving CD45RB$^{lo}$ T cells from saline-treated animals (*P<0.001). Right panel: Treatment with IL-10 specific antibody abrogates protection transferred by Treg cells harvested from CP1-treated animals. CD45RB$^{lo}$ T cells from CP1-treated mice were transferred to naïve recipient animals that were treated one day later with a monoclonal antibody specific for IL-10 or an isotype control antibody. Mice receiving Treg cells that were treated with the isotype control antibody had few adhesions. However, the protection conferred by the transfer of Treg cells to mice was abrogated by treatment with IL-10-specific antibody (*P=0.0002 compared with isotype control treatment).

Example 3

Role of ICOS-ICOSL Interactions in Protection Conferred by Treg Cells

Figure 3A:
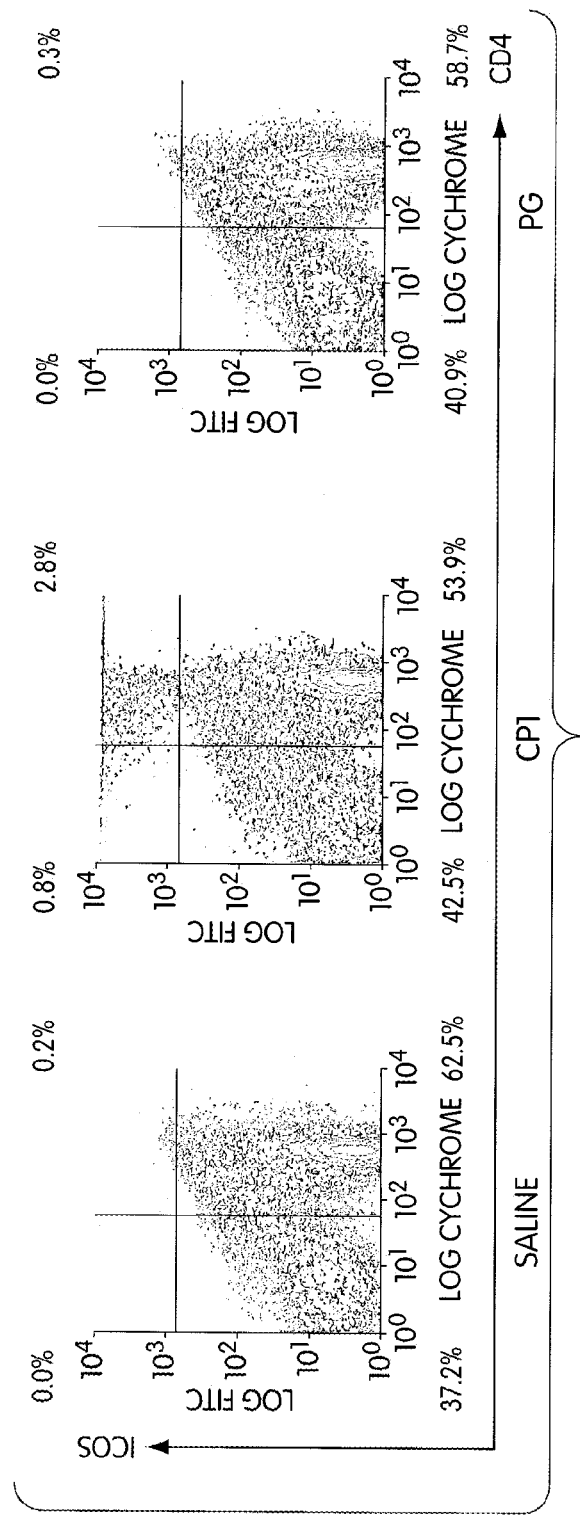
FIG. 3A is a series of three graphs depicting results of flow cytometry analysis for expression of ICOS by CD4+ T cells following in vivo administration of saline, CP1, or PG.

FIG. 3A shows that CP1 induces ICOS expression on CD4+ T cells in vivo. Mice were treated with CP1 or PG as described above and splenic T cells isolated and stained for ICOS and CD4 expression. CP1 induced the expression of ICOS on CD4+ T cells and peaked 4 days following the final dose. PG did not elicit ICOS expression on these cells.

Figure 3B:
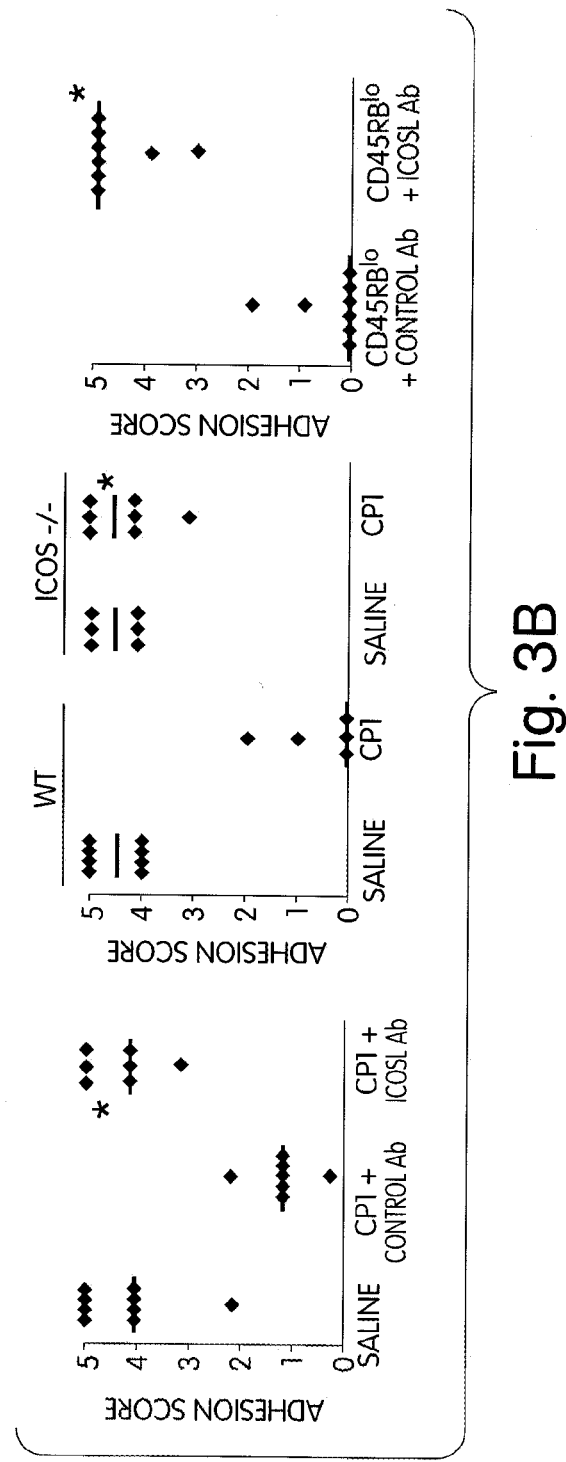
FIG. 3B is a series of three graphs depicting the role of ICOS-ICOSL interaction in adhesion score. *P=0.0006

The left panel of FIG. 3B shows that ICOSL antibody abrogates protection by CP1. Mice were treated with saline or CP1 prior to the induction of adhesions. CP1-treated mice were also given a monoclonal antibody specific for ICOSL (400 μg/mouse) or an isotype control antibody via the intraperitoneal route 0, 48, and 96 hours relative to surgery. Mice treated with CP1 and the isotype control antibody had significantly fewer and less severe adhesions compared with mice treated with the monoclonal antibody specific for ICOSL (P=0.0003 compared with isotype control treatment).

The middle panel of FIG. 3B shows that ICOS$^{-/-}$ mice are not protected by CP1 treatment. WT and ICOS$^{-/-}$ mice were treated with saline or CP1 as described above prior to the induction of adhesions. ICOS$^{-/-}$ animals treated with CP1 had lower adhesion scores compared with similarly treated WT animals (P=0.002).

The right panel of FIG. 3B shows that ICOSL antibody abrogates protection by Treg cells from CP1-treated mice. C57BL/6 mice were treated with CP1 as described above and CD45RB$^{lo}$ CD4+ T cells harvested from spleens one day later by FACS. Treg cells were transferred to two groups of naïve C57BL/6 mice via the intracardiac route and 24 hours later animals were subjected to cecal abrasion surgery. Recipient animals received the ICOSL-specific antibody or the isotype control antibody (400 μg/mouse) via the intraperitoneal route 0, 48, and 96 hours relative to surgery. Each group of animals was evaluated six days later for adhesions. Treatment with ICOSL antibody abrogated protection conferred by the transfer of Treg cells compared with treatment with an isotype control antibody (P=0.0006).

Example 4

Treg Cells Produce IL-10 in Response to CP1 in an ICOS-Dependent Manner

Figure 4A:
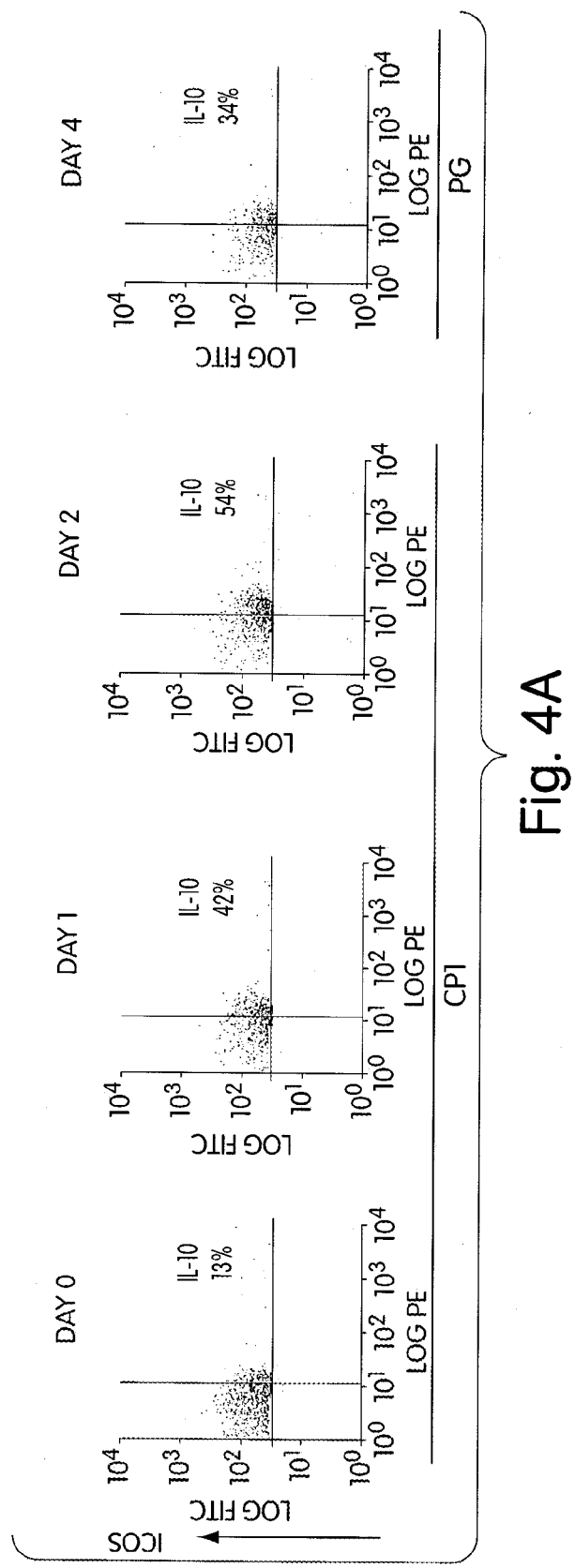
FIG. 4A is a series of graphs depicting results of flow cytometry analysis for IL-10 production by ICOS+ Treg cells following treatment with CP1 or PG.

FIG. 4A shows IL-10 production by ICOS+ Treg cells. C57BL/6 mice were treated with CP1 or PG as described above and CD45RB$^{lo}$ T cells isolated at different time points following the last dose. Cells were stained for ICOS surface expression and intracellular IL-10 production and gated on CD4 T cells for analysis. Treatment with CP1 elicited IL-10 production from ICOS+ Treg cells. This response was substantially higher than IL-10 produced by Treg cells from PG-treated mice. ICOS− Treg cells from CP1-treated mice did not produce IL-10.

Figure 4B:
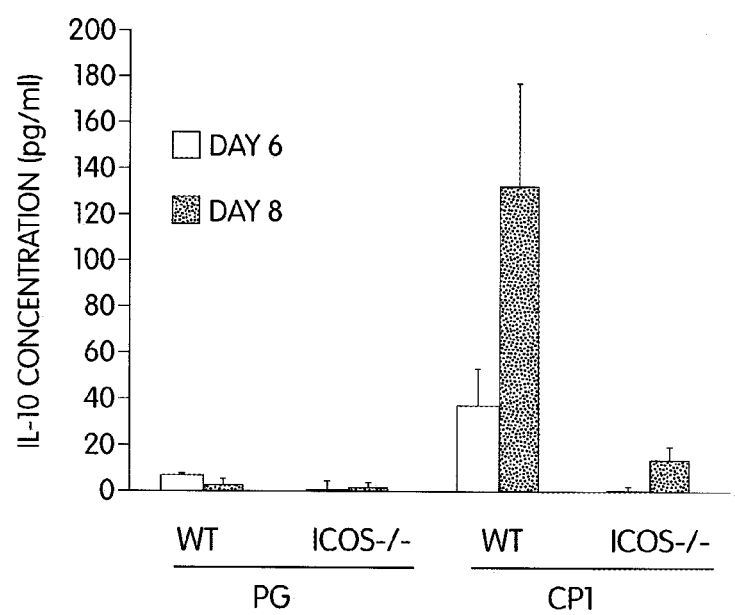
FIG. 4B is a graph depicting IL-10 production by Treg cells obtained from wildtype (WT) and ICOS$^{-/-}$ mice following treatment with CP1 or PG.

FIG. 4B shows that IL-10 production by Treg cells is specific for CP1 and is dependent on ICOS. WT and ICOS$^{-/-}$ mice were treated with CP1 (50 μg via the subcutaneous route) and ten days later CD45RB$^{lo}$ T cells isolated and co-cultured with irradiated autologous antigen presenting cells in vitro. Cells were stimulated with CP1 or PG (20 μg/ml) and culture supernates harvested 6 or 8 days post-culture for IL-10 quantitation by ELISA. Treg cells from WT mice stimulated with CP1 yielded higher levels of IL-10 than Treg cells from ICOS$^{-/-}$ mice. This response was specific to CP1 since PG did not elicit IL-10 from WT or ICOS$^{-/-}$ Treg cells. Treg cells from animals treated with PG in vivo that were stimulated by this polymer in vitro did not produce IL-10 in these assays.

Example 5

PSA can Ameliorate Asthma

In order to assess the ability of zwitterionic polysaccharide to prevent asthma, PSA is tested in an established mouse model of allergic asthma. Mojtabavi N et al. (2002) *J Immunol* 169:4788-96. Four groups of female BALB/c mice (8 mice per group) are sensitized and challenged with ovalbumin (OVA) to induce experimental asthma. Assigned experimental groups of mice are treated with aerosolized or subcutaneous injection of PSA. Assigned control groups of mice receive no treatment or are treated with subcutaneous injection of saline. Animal groups and experimental design are shown in Table 1.

Sensitizations for all mice involve intraperitoneal (i.p.) injection of 200 μg OVA in 4 ml saline on day 0, followed by an identical boost on day 21. Aerosol treatment with PSA in Group B mice involves thrice-weekly administration of 500 μg aerosolized 0.01% PSA (0.1 mg/ml) by ultrasonic nebulizer during days 1-27. Subcutaneous treatment with PSA in Group C involves 100 μl subcutaneous (s.c.) injection of 0.1% PSA (1 mg/ml solution of PSA) administered on the same schedule as the aerosol treatment.

TABLE 1

Asthma Model Protocol

| Group | Sensitization Day 0 | Treatment Days 1-27 | Boost Day 21 | Challenge Days 28-29 |
|---|---|---|---|---|
| A | 10 µg OVA in 200 µl i.p. | none | 10 µg OVA in 200 µl i.p. | 1% OVA aerosol |
| B | 10 µg OVA in 200 µl i.p. | aerosol PSA 500 µg/5 ml | 10 µg OVA in 200 µl i.p. | 1% OVA aerosol |
| C | 10 µg OVA in 200 µl i.p. | 100 µg PSA in 100 µl s.c. | 10 µg OVA in 200 µl i.p. | 1% OVA aerosol |
| D | 10 µg OVA in 200 µl i.p. | saline 100 µl s.c. | 10 µg OVA in 200 µl i.p. | 1% OVA aerosol |

Challenge for all mice involves aerosol administration of 1% OVA (1 g/100 ml) by ultrasonic nebulizer for 60 minutes twice daily on days 28 and 29.

Animals are sacrificed 48-96 hours following the last aerosol challenge and are evaluated for lung histopathology, serum OVA-specific IgE, and bronchoalveolar lavage (BAL) fluid IL-4, IL-5, and IL-10.

For measurement of OVA-specific IgE, ELISA plates are coated with anti-mouse IgE (LO-ME-3; Serotec, Oxford, U.K.) at 10 µg/ml overnight at 4° C. The plates are washed and blocked with 2% BSA/0.05% Tween 20 for 2 hours at 37° C. Titrated sera are incubated for 2 hours at room temperature. After washing, biotinylated OVA is added, and plates are incubated for 1 hour. Europium ($Eu^{3+}$)-streptavidin (Delfia; Wallac, Turku, Finland) is added to each well after the plates are washed. Enhancement solution (100 µl; Delfia) is added, and $Eu^{3+}$ release is measured by fluorimetry at 340 nm excitation and 614 nm emission.

For measurement of BAL fluid cytokines, tracheas of lethally anesthetized mice are cannulated and lavaged one to three times with 1 ml of PBS. BAL fluid from each mouse is pooled and IL-4, IL-5, and IL-10 are quantitated using ELISA assays (Endogen, Woborn, Mass.), following the manufacturer's instructions.

For lung histopathology, following BAL, tracheas are perfused with PBS and then 4% formalin. Paraffin-embedded lung sections of 4 µm are stained with H&E for morphological staining and with periodic acid-Schiff for mucopolysaccharide staining.

Airway hyperresponsiveness (AHR) is measured in conscious, unrestrained mice by whole-body plethysmography (Buxco Electronics, Sharon, Conn.) using a published method. Hamelmann E et al. (1997) *Am J Respir Crit Care Med* 156:766-75.

Example 6

Zwitterionic Peptides Induce T Cell Activation

In order to demonstrate the role of the zwitterionic charge motif in T cell activation, a dipeptide repeating unit was synthesized to mimic the repeating unit structure of PSA. For this purpose, different repeating unit sizes of lysine (K) and aspartic acid (D), $(K-D)_n$, were synthesized and tested for their ability to stimulate CD4+ T cells.

Peptides $(K-D)_n$ were synthesized on a Rainin Symphony peptide synthesizer with 4-alkoxybenzyl alcohol (PAC) resins (PerSeptive Biosystems, Inc., Framingham, Mass.) using Fmoc chemistry. Amino acids were activated with 2-(1H-benzotriazole-1-yl)-1,3,3 tetramethyluronium hexafluorophosphate (HBTU) for coupling. The peptides prepared were analyzed by matrix-assisted laser desorption ionization-time-of-flight (MALDI-TOF) mass spectrometry and nuclear magnetic resonance (NMR) spectroscopy. Mass spectra were acquired on a Voyager MALDI-TOF mass spectrometer. Proton NMR spectra were acquired on a Brucker AMX500 instrument with proton frequency of 500 MHz. Both analyses confirmed that the peptides were the expected structures.

T cell proliferation assays were performed on cells obtained from human leukopacs (discarded white cells from anonymous platelet donors). Mononuclear cells were separated by ficoll-hypaque sedimentation to eliminate red cells and polymorphonuclear leukocytes. The mononuclear layer, which consisted of T cells, B cells, and mononuclear cells, was depleted of B cells and monocytes by passage over nylon wool column. A portion of these cells was saved prior to placement on nylon wool and were used as autologous feeder cells following irradiation with 6.4 kRads with a cesium source for 4.8 min. Nylon-passed cells, which were greater than 98% CD3 positive (as determined by FACS analysis) were used as responder cells or further depleted with antibodies to CD4 (OKT4) or CD8 (OKT8) followed by negative selection with magnetic beads. Finberg R W et al. (1992) *J Immunol* 149:2055-60; Haregewoin A et al. (1989) *Nature* 340:309-12. $(K-D)_n$ peptides (20 µg/ml) of varying size were added to human T cells ($5 \times 10^4$ cells/200 µl) co-cultured with irradiated APCs ($2.5 \times 10^5$/200 µl) for 12 days in U-bottom 96 well plates (Corning-Costar Corp., Cambridge, Mass.) with RPMI 1640 and 5% fetal calf serum. Nguyen L H et al. (1992) *J Virol* 66:7067-72. The *S. pneumoniae* type 1 CP (20 µg/ml) was included as a positive control. Six days later, cells were pulsed with 1 mCi of $^3$H-thymidine/well 6 h prior to harvest in order to measure cell proliferation. Cells were washed extensively, harvested, and the amount of radioactive uptake counted by liquid scintillation. Data were expressed as the average of triplicate wells ± the standard error of cpm represented.

$(K-D)_n$ peptides consisting of 15, 20, or 25 repeating units each stimulated T cell activation in vitro. The response was less with peptides of 10 repeats. Peptides consisting of less than 10 repeating units (1 and 5 repeats) did not stimulate T cell activation. A control peptide, poly-L-lysine, also did not stimulate T cell proliferation. These data clearly indicate that zwitterionic repeating unit polymers other than polysaccharides stimulate T cell activation and that this activity depends on the repeating unit size of the polymer.

Example 7

Zwitterionic Peptides $(K-D)_n$ can Ameliorate Asthma

In order to assess the ability of zwitterionic oligopeptide to prevent asthma, the protocol of Example 5 is followed, substituting $(K-D)_n$ for PSA, wherein n is an integer between 10 and 25.

Example 8

CP1 can Ameliorate Asthma

In order to assess the ability of zwitterionic polysaccharide to prevent asthma, CP1 was tested in an established mouse model of allergic asthma. Mojtabavi N et al. (2002) *J Immunol* 169:4788-96. Three groups of female BALB/c mice (8 mice per group) were sensitized with ovalbumin (OVA; 10 µg in alum, i.p.) and boosted with this same dose 21 days later. Beginning seven days after the boost, mice were challenged with aerosolized OVA (1% OVA 60 minutes twice a day for two days) or saline (60 minutes twice a day for two days). Two days after the last challenge serum was collected from blood obtained by cardiac puncture and the mice were sacrificed for evaluation of lung histopathology, OVA-specific serum IgE, and serum IL-13. Throughout the course of the experiment individual groups of mice were administered CP1 (100 μg in 100 μl s.c. three times a week) or saline (100 μl s.c. three times a week). A fourth group of 8 mice was not sensitized and received saline treatment and saline challenge. Animal groups and experimental design are shown in Table 2.

TABLE 2

Asthma Model Protocol

| Group | Sensitization Day 0 | Treatment Days 1-27 | Boost Day 21 | Challenge Days 28-29 |
|---|---|---|---|---|
| A | none | saline | none | saline aerosol |
| B | OVA | CP1 | OVA | 1% OVA aerosol |
| C | OVA | saline | OVA | 1% OVA aerosol |
| D | OVA | saline | OVA | saline aerosol |

For measurement of OVA-specific IgE, ELISA plates were coated with anti-mouse IgE (LO-ME-3; Serotec, Oxford, U.K.) at 10 μg/ml overnight at 4° C. The plates were washed and blocked with 2% BSA/0.05% Tween 20 for 2 hours at 37° C. Titrated sera were incubated for 2 hours at room temperature. After washing, biotinylated OVA was added, and plates were incubated for 1 hour. Europium ($Eu^{3+}$)-streptavidin (Delfia; Wallac, Turku, Finland) was added to each well after the plates were washed. Enhancement solution (1004 Delfia) was added, and $Eu^{3+}$ release was measured by fluorimetry at 340 nm excitation and 450 nm emission.

IL-13 was measured using an IL-13-specific ELISA (R and D Systems).

For lung histopathology, tracheas were perfused with PBS and then 4% formalin. Paraffin-embedded lung sections of 4 μm were stained with hematoxylin and eosin for morphological staining and with periodic acid-Schiff (PAS) for mucopolysaccharide staining.

Representative results are shown in FIGS. 5-8.

Figure 5:
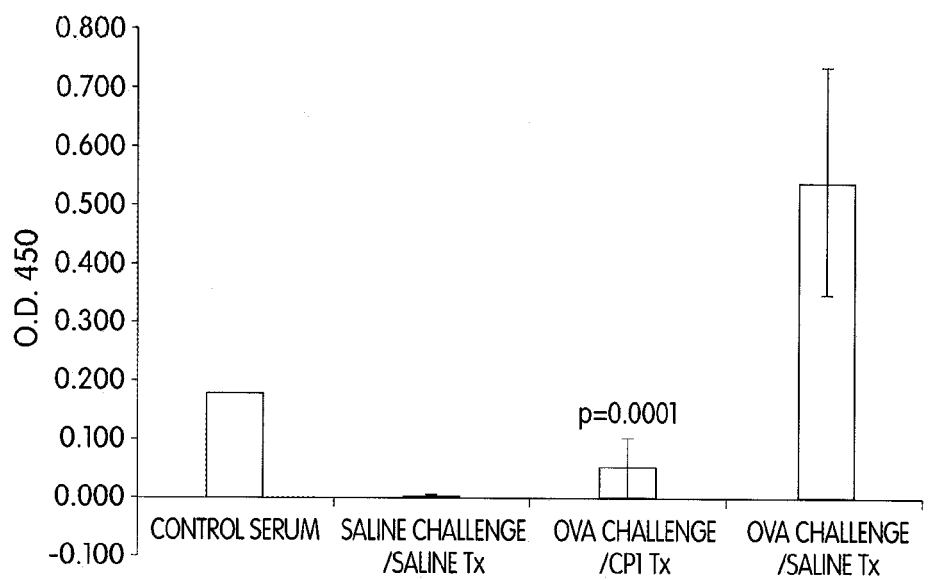
FIG. 5 is a bar graph depicting antigen-specific serum IgE levels in antigen-sensitized mice challenged with aerosolized antigen, following treatment with CP1 or control (saline). Mice (N=8 per group) treated with CP1 had a significant reduction in antigen-specific IgE compared with mice treated with saline (p=0.0001).

As shown in FIG. 5, CP1 treatment reduced OVA-specific IgE levels in mice with airway hyperreactivity. OVA-sensitized, OVA-challenged mice treated with CP1 had significantly reduced OVA-specific serum IgE compared with OVA-sensitized, OVA-challenged mice treated with saline (p=0.0001 by Fisher's Exact test). In fact, OVA-sensitized, OVA-challenged mice treated with CP1 had OVA-specific serum IgE levels that were more similar to those of unsensitized, saline-challenged mice treated with saline than to those of OVA-sensitized, saline-challenged mice treated with saline.

Figure 6:
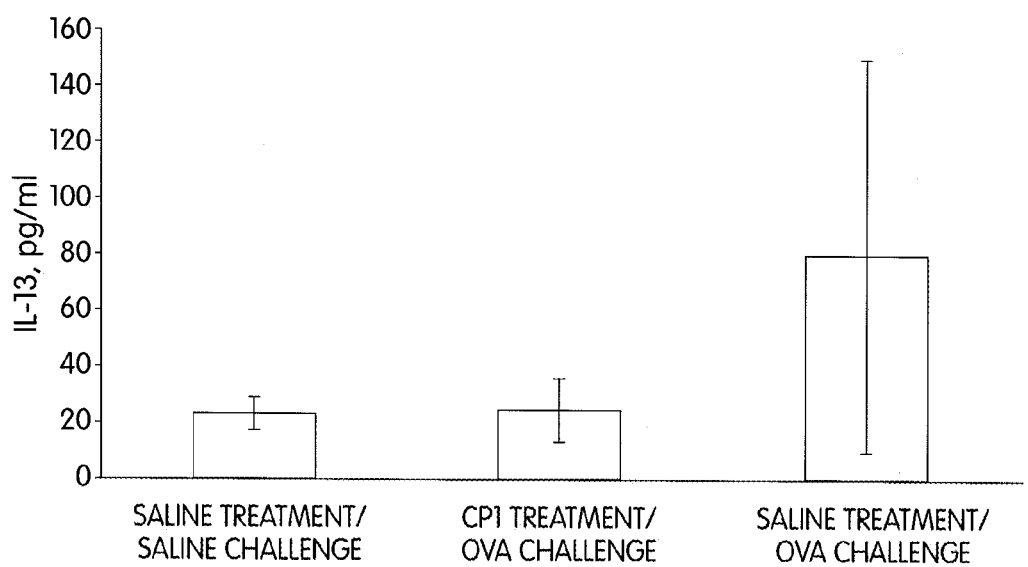
FIG. 6 is a bar graph depicting serum IL-13 levels in antigen-sensitized mice challenged with aerosolized antigen, following treatment with CP1 or control (saline). Mice (N=8 per group) treated with CP1 had a reduction in serum IL-13 compared with mice treated with saline.

As shown in FIG. 6, CP1 treatment reduced serum IL-13 levels in mice with airway hyperreactivity. OVA-sensitized, OVA-challenged mice treated with CP1 had significantly reduced serum IL-13 compared with OVA-sensitized, OVA-challenged mice treated with saline (p=0.03 by Tukey-Kramer Multiple Comparisons test). In fact, OVA-sensitized, OVA-challenged mice treated with CP1 had serum IL-13 levels that were essentially the same as those of unsensitized, saline-challenged mice treated with saline.

Figure 7A:
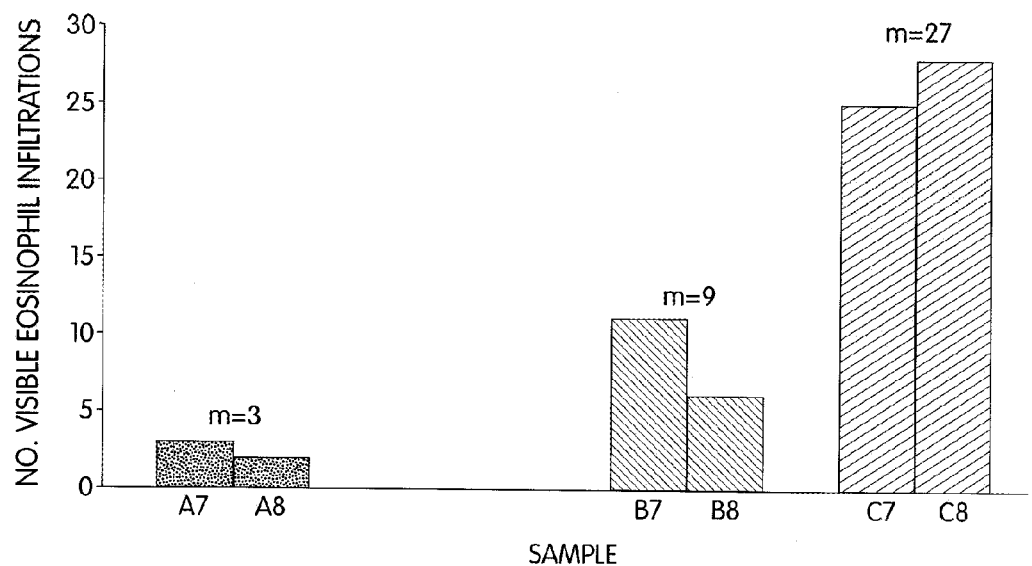
FIG. 7A is a bar graph depicting eosinophil infiltration in lung sections obtained from antigen-sensitized mice challenged with aerosolized antigen, following treatment with CP1 or control (saline). Each bar represents results from a single mouse. Mice (N=8 per group) treated with CP1 had a reduction in eosinophil infiltrations compared with mice treated with saline.
Figure 7B:
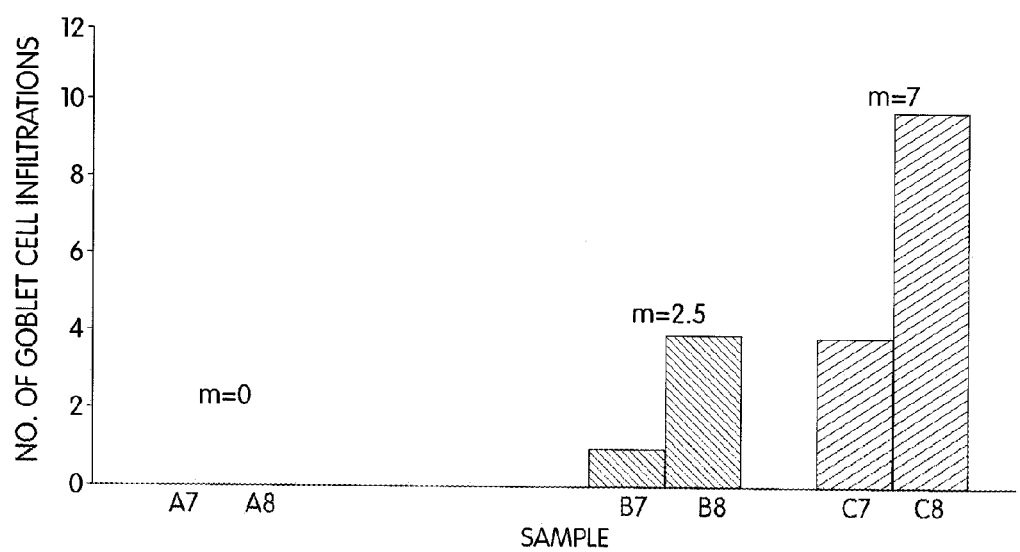
FIG. 7B is a bar graph depicting goblet cell infiltration in lung sections obtained from antigen-sensitized mice challenged with aerosolized antigen, following treatment with CP1 or control (saline). Each bar represents results from a single mouse. Mice (N=8 per group) treated with CP1 had a reduction in goblet cell infiltrations compared with mice treated with saline.
Figure 8:
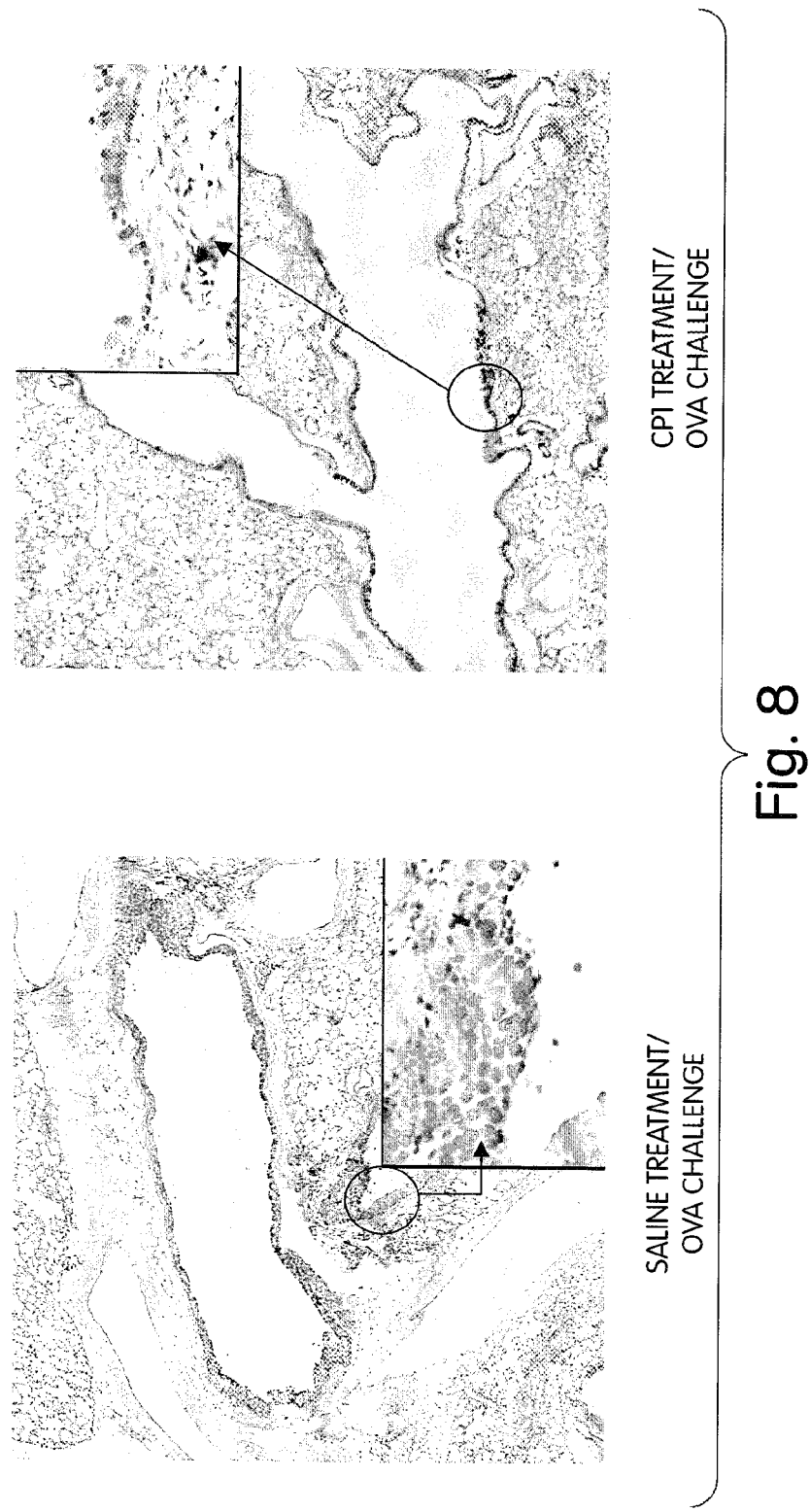
FIG. 8 is a pair of photomicrographs depicting goblet cell infiltration lining bronchioles in lung sections obtained from antigen-sensitized mice challenged with aerosolized antigen, following treatment with CP1 (right panel) or control (saline; left panel). CP1-treated mice had fewer areas of goblet cell infiltration than saline-treated mice.

As shown in FIG. 7, treatment with CP1 reduced eosinophil infiltration and goblet cell infiltration, each associated with airway hyperreactivity. Examination of two mice in each of groups A, B, and C (see Table 2) revealed the presence of at least twice as many eosinophil infiltrations in the OVA-sensitized, OVA-challenged group treated with saline as in the corresponding group treated with CP1 (FIG. 7A). Similarly, examination of the same two mice in each of groups A, B, and C (see Table 2) revealed the presence of at least twice as many goblet cell infiltrations in the OVA-sensitized, OVA-challenged group treated with saline as in the corresponding group treated with CP1 (FIG. 7B). FIG. 8 shows representative PAS-stained sections from OVA-sensitized, OVA-challenged mice treated with saline (left panel) and from OVA-sensitized, OVA-challenged mice treated with CP1 (right panel). CP1-treated mice had fewer areas of goblet cell infiltration than saline-treated mice.

Example 9

Expansion of Treg Cells In Vitro

Naive splenic $CD4^+$ T cells from mice were obtained and cultured in 96-well plates with autologous irradiated antigen presenting cells (APCs). T cells and APCs were each added to individual wells at $2\times10^5$ cells/well. The cells were cultured with 20 μg/ml of zwitterionic polysaccharide (ZPS) PSA, IL-2 (0.5 ng/ml), and IL-15 (10 ng/ml each) for one week. After one week, fresh APCs, cytokines, and polysaccharide were added at the concentrations above. This cycle was repeated for a total of three times. Following this procedure, ZPS-specific Treg cells with a $CD45RB^{lo}$ phenotype that made IL-10 in response to ZPS stimulation were found to predominate (50 percent of cells in well). IL-10 was measured by intracellular cytokine staining with flow cytometry.

Example 10

Intracellular Cytokine Analysis

After preincubation with rat anti-mouse CD16/CD32 to block Fc receptors, T cells were stained with FITC-, PE-Cy5-, or PE-labeled mAbs to CD4, CD45RB, or ICOS or the corresponding isotype control antibodies. Intracellular cytokine analysis was performed as previously described. Akbari O et al. (2002) *Nat Med.* 8:1024-32. In brief, cells were washed, fixed, and permeabilized with Cytofix/Cytoperm solution and 1' Perm/Wash solution (BD Pharmingen, San Diego, Calif., USA) and then stained with PE-Cy5- or PE-conjugated monoclonal antibodies specific for IL-4, IFN-γ, or IL-10 or the corresponding isotype controls. Stained cells were analyzed on a Coulter EPICS XL™ cytometer (Beckman Coulter), using the CELLQuest™ (Becton Dickinson), and WinMDI 2.8 analysis software (Scripps Research Institute. All antibodies were obtained from BD PharMingen (San Diego, Calif.).

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for treating asthma in a subject, comprising:
   administering to a subject having asthma an isolated polymer in an effective amount to treat the asthma,
   wherein the polymer is *B. fragilis* polysaccharide A (PSA).

2. The method of claim 1, wherein the subject is free of symptoms otherwise calling for treatment with the polymer.

3. The method of claim 1, wherein the administering comprises delivering an aerosol of the polymer to an airway of the subject.

4. The method of claim 1, wherein the method further comprises administering to the subject an anti-asthma medicament selected from the group consisting of glucocorticoids, beta adrenergic agonists, methylxanthines, anticholinergics, cromolyn, nedocromil, antihistamines, and anti-IgE.

5. The method of claim 1, wherein the administering comprises administering to the subject multiple doses of the isolated polymer to treat asthma.

6. A method for treating a subject having asthma associated with an identified allergen, comprising
   (a) administering an allergen to a subject having asthma associated with the allergen; and
   (b) administering to the subject a polymer in an effective amount to treat the asthma,
   wherein the polymer is *B. fragilis* polysaccharide A (PSA).

7. The method of claim 6, wherein the allergen is administered before PSA.

8. The method of claim 6, wherein the allergen is administered after PSA.

9. The method of claim 6, wherein the allergen and PSA are administered substantially contemporaneously.

\* \* \* \* \*